(12) United States Patent
Douglas et al.

(10) Patent No.: US 12,174,601 B2
(45) Date of Patent: Dec. 24, 2024

(54) BUILDING SYSTEM WITH OCCUPANT HEALTH ANALYSIS BASED ON WATER USAGE

(71) Applicant: Johnson Controls Tyco IP Holdings LLP, Milwaukee, WI (US)

(72) Inventors: Jonathan D. Douglas, Mequon, WI (US); Terrill R. Laughton, Milwaukee, WI (US); Rachel D. M. Ellerman, Shorewood, WI (US); Kirk H. Drees, Cedarburg, WI (US)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 512 days.

(21) Appl. No.: 17/525,227

(22) Filed: Nov. 12, 2021

(65) Prior Publication Data

US 2023/0152760 A1 May 18, 2023

(51) Int. Cl.
| | | |
|---|---|---|
| *G05B 15/02* | (2006.01) | |
| *A61L 2/10* | (2006.01) | |
| *G16H 10/60* | (2018.01) | |
| *G16H 40/20* | (2018.01) | |
| *G16H 50/30* | (2018.01) | |

(Continued)

(52) U.S. Cl.
CPC ............ *G05B 15/02* (2013.01); *A61L 2/10* (2013.01); *G16H 10/60* (2018.01); *G16H 40/20* (2018.01); *G16H 50/30* (2018.01); *G16H 50/70* (2018.01); *G16H 50/80* (2018.01); *A61L 2202/11* (2013.01); *A61L 2202/14* (2013.01)

(58) Field of Classification Search
CPC ... G05B 15/02; G05B 2219/2642; A61L 2/10; A61L 2202/11; A61L 2202/14; A61L 2/18; A61L 2/22; A61L 2202/25; G16H 10/60; G16H 40/20; G16H 50/30; G16H 50/70; G16H 50/80
See application file for complete search history.

(56) References Cited

U.S. PATENT DOCUMENTS

| | | | |
|---|---|---|---|
| 2014/0142904 A1* | 5/2014 | Drees | G06Q 10/04 703/2 |
| 2016/0284200 A1* | 9/2016 | Song | G08B 21/182 |
| 2017/0124838 A1* | 5/2017 | Sinha | H04W 64/003 |

(Continued)

OTHER PUBLICATIONS

Alvarado et al., "A Methodology to Monitor Airborne PM10 Dust Particles Using a Small Unmanned Aerial Vehicle," Sensors, 2017, vol. 17 (25 pages).

*Primary Examiner* — Christopher E. Everett
*Assistant Examiner* — Istiaque Ahmed
(74) *Attorney, Agent, or Firm* — Foley & Lardner LLP

(57) ABSTRACT

A building system of a building including one or more memory devices storing instructions thereon that, when executed by one or more processors, cause the one or more processors to receive water usage data from one or more network connected water valves, the water usage data indicating water usage by one or more occupants within the building. The instructions cause the one or more processors to derive one or more health metrics indicating physical health of the one or more occupants based on the water usage data and cause one or more pieces of building equipment to perform one or more operations based on values of the one or more health metrics, the one or more operations improving the physical health of the one or more occupants.

20 Claims, 10 Drawing Sheets

(51) Int. Cl.
*G16H 50/70* (2018.01)
*G16H 50/80* (2018.01)

(56) References Cited

U.S. PATENT DOCUMENTS

| | | | |
|---|---|---|---|
| 2018/0144418 A1* | 5/2018 | Ravid | G01M 3/2807 |
| 2019/0090859 A1* | 3/2019 | Recht | A61B 10/007 |
| 2019/0138512 A1 | 5/2019 | Pourmohammad et al. | |
| 2020/0184792 A1 | 6/2020 | Pourmohammad et al. | |
| 2021/0200170 A1 | 7/2021 | Ploegert et al. | |
| 2021/0313075 A1 | 10/2021 | Mc Namara et al. | |
| 2021/0375440 A1* | 12/2021 | Schlameuss | G01N 33/18 |
| 2022/0028533 A1* | 1/2022 | Kulkarni | G16H 50/80 |
| 2022/0034542 A1* | 2/2022 | Peters | F24F 11/0001 |
| 2022/0092298 A1* | 3/2022 | Madden | G06T 7/0004 |
| 2022/0203287 A1 | 6/2022 | Wenger et al. | |
| 2022/0203288 A1 | 6/2022 | Wenger et al. | |
| 2022/0205962 A1 | 6/2022 | Vanderkoy | |
| 2022/0207215 A1 | 6/2022 | Liu et al. | |
| 2022/0221184 A1 | 7/2022 | Gupta et al. | |
| 2022/0228756 A1 | 7/2022 | Gupta et al. | |
| 2022/0254483 A1 | 8/2022 | Boisvert et al. | |
| 2022/0277851 A1 | 9/2022 | Wellig | |
| 2022/0282886 A1 | 9/2022 | Hriljac et al. | |
| 2022/0293261 A1 | 9/2022 | McBrady et al. | |
| 2022/0305438 A1 | 9/2022 | Wenger et al. | |
| 2022/0305881 A1 | 9/2022 | Neu et al. | |
| 2023/0089131 A1* | 3/2023 | Nasis | F24F 11/65 454/68 |

\* cited by examiner

BUILDING SYSTEM WITH OCCUPANT HEALTH ANALYSIS BASED ON WATER USAGE

BACKGROUND

The present disclosure relates to building systems of a building. The present disclosure relates more particularly to health of the building.

In some embodiments, a building includes various building systems that operate to provide environmental control, security, fire response, and various other services for a building. However, based on the operation of the building systems, the performance of building spaces may change based on the operation of the building systems, i.e., whether the building systems are operating correctly or have encountered errors. Users may occupy the spaces of the building. The mental and physical wellbeing of users may be based on the operation of the building systems and/or services offered within the building. Furthermore, the operation of the building systems may affect energy usage and pollution generation, affecting the environment surrounding the building.

SUMMARY

One implementation of the present disclosure is a building system of a building including one or more memory devices storing instructions thereon that, when executed by one or more processors, cause the one or more processors to receive water usage data from one or more network connected water valves, the water usage data indicating water usage by one or more occupants within the building. The instructions cause the one or more processors to derive one or more health metrics indicating physical health of the one or more occupants based on the water usage data and cause one or more pieces of building equipment to perform one or more operations based on values of the one or more health metrics, the one or more operations improving the physical health of the one or more occupants.

In some embodiments, the instructions cause the one or more processors to receive an occupancy level indicating a number of the one or more occupants from an occupancy system that tracks occupancy levels of the building and derive the one or more health metrics indicating the physical health of the one or more occupants based on the water usage data and the occupancy level.

In some embodiments, the instructions cause the one or more processors to determine a number of the one or more occupants with an occupancy model based on the water usage data, wherein the occupancy model correlates a level of the water usage data with the number of the one or more occupants.

In some embodiments, the instructions cause the one or more processors to determine an infectious disease risk level for the building based on the one or more health metrics indicating the physical health of the one or more occupants, the infectious disease risk level indicating a level of risk of contracting an infectious disease within the building.

In some embodiments, the instructions cause the one or more processors to identify a first portion of the water usage data associated with a first area of the building, identify a second portion of the water usage data associated with a second area of the building, derive one or more first health metrics indicating physical health of the one or more occupants associated with the first area of the building, derive one or more second health metrics indicating the physical health of the one or more occupants associated with the second area of the building, and cause a display device of a user device to include information associated with the one or more first health metrics and the one or more second health metrics.

In some embodiments, the instructions cause the one or more processors to receive occupancy data identifying a first occupant and a second occupant, identify, based on the occupancy data, first water usage data associated with the first occupant and second water usage data associated with the second occupant, derive a first health metric indicating physical health of the first occupant based on the first water usage data, derive a second health metric indicating physical health of the second occupant based on the first water usage data, and cause a display device of a user device to include information associated with the first health metric and the second health metric.

In some embodiments, the one or more health metrics include a handwashing cleanliness metric. In some embodiments, the instructions cause the one or more processors to determine the handwashing cleanliness metric by identifying a number of toilet or urinal flushes based on the water usage data, wherein at least one of the one or more network connected water valves are configured to flush water on a toilet or urinal of a bathroom of the building, identifying a number of hand washes based on the water usage data, wherein at least one of the one or more network connected water valves are configured to run water at a handwashing sink of the bathroom, and comparing the number of toilet or urinal flushes to the number of hand washes to determine the handwashing cleanliness metric.

In some embodiments, the instructions cause the one or more processors to schedule cleaning for one or more particular areas of the building based on the one or more health metrics and send a notification of scheduled cleaning to a user device of one or more cleaning personal.

In some embodiments, the instructions cause the one or more pieces of building equipment to perform the one or more operations based on the values of the one or more health metrics by determining that the values of the one or more health metrics are below a level and causing an air handler unit of the building to increase a level of clean air changes of the building responsive to determining that the values of the one or more health metrics are below the level.

In some embodiments, the instructions cause the one or more pieces of building equipment to perform the one or more operations based on the values of the one or more health metrics by determining that the values of the one or more health metrics are below a level and causing an ultraviolet light system of the building to activate and disinfect one or more surfaces of objects of the building responsive to determining that the values of the one or more health metrics are below the level.

In some embodiments, the one or more health metrics include an occupant hydration metric. In some embodiments, the instructions cause the one or more processors to determine the occupant hydration metric by identifying a number of toilet or urinal flushes based on the water usage data, wherein at least one of the one or more network connected water valves are configured to flush water on a toilet or urinal of a bathroom of the building and identifying the occupant hydration metric based on a number of occupants within the building and the number of toilet or urinal flushes.

In some embodiments, the instructions cause the one or more processors to identify a number of water drinking fountain runs based on the water usage data, wherein at least one of the one or more network connected water valves are configured to cause water to run at a water drinking fountain and identify the occupant hydration metric further based on the number of water drinking fountain runs.

Another implementation of the present disclosure is a method of a building system of a building including receiving, by a processing circuit, water usage data from one or more network connected water valves, the water usage data indicating water usage by one or more occupants within the building. The method further includes deriving, by the processing circuit, one or more health metrics indicating physical health of the one or more occupants based on the water usage data and causing, by the processing circuit, one or more pieces of building equipment to perform one or more operations based on values of the one or more health metrics, the one or more operations improving the physical health of the one or more occupants.

In some embodiments, the method further includes determining, by the processing circuit, an infectious disease risk level for the building based on the one or more health metrics indicating the physical health of the one or more occupants, the infectious disease risk level indicating a level of risk of contracting an infectious disease within the building.

In some embodiments, the method further includes identifying, by the processing circuit, a first portion of the water usage data associated with a first area of the building, identifying, by the processing circuit, a second portion of the water usage data associated with a second area of the building, deriving, by the processing circuit, one or more first health metrics indicating the physical health of the one or more occupants associated with the first area of the building, deriving, by the processing circuit, one or more second health metrics indicating the physical health of the one or more occupants associated with the second area of the building, and causing, by the processing circuit, a display device of a user device to include information associated with the one or more first health metrics and the one or more second health metrics.

In some embodiments, the method further includes receiving, by the processing circuit, occupancy data identifying a first occupant and a second occupant, identifying, by the processing circuit, based on the occupancy data, first water usage data associated with the first occupant and second water usage data associated with the second occupant, deriving, by the processing circuit, a first health metric indicating physical health of the first occupant based on the first water usage data, deriving, by the processing circuit, a second health metric indicating physical health of the second occupant based on the first water usage data, and causing, by the processing circuit, a display device of a user device to include information associated with the first health metric and the second health metric.

In some embodiments, the one or more health metrics include a handwashing cleanliness metric. In some embodiments, causing, by the processing circuit, the one or more processors to determine the handwashing cleanliness metric includes identifying a number of toilet or urinal flushes based on the water usage data, wherein at least one of the one or more network connected water valves are configured to flush water on a toilet or urinal of a bathroom of the building, identifying a number of hand washes based on the water usage data, wherein at least one of the one or more network connected water valves are configured to run water at a handwashing sink of the bathroom, and comparing the number of toilet or urinal flushes to the number of hand washes to determine the handwashing cleanliness metric.

In some embodiments, the method includes scheduling, by the processing circuit, cleaning for one or more particular areas of the building based on the one or more health metrics and sending, by the processing circuit, a notification of scheduled cleaning to a user device of one or more cleaning personal.

In some embodiments, the method includes causing, by the processing circuit, the one or more pieces of building equipment to perform the one or more operations based on the values of the one or more health metrics includes determining that the values of the one or more health metrics are below a level and causing an air handler unit of the building to increase a level of clean air changes of the building responsive to determining that the values of the one or more health metrics are below the level.

In some embodiments, causing, by the processing circuit, the one or more pieces of building equipment to perform the one or more operations based on the values of the one or more health metrics includes determining that the values of the one or more health metrics are below a level and causing an ultraviolet light system of the building to activate and disinfect one or more surfaces of objects of the building responsive to determining that the values of the one or more health metrics are below the level.

In some embodiments, the one or more health metrics include an occupant hydration metric. In some embodiments, the method further includes determining, by the processing circuit, the occupant hydration metric by identifying a number of toilet or urinal flushes based on the water usage data, wherein at least one of the one or more network connected water valves are configured to flush water on a toilet or urinal of a bathroom of the building and identifying the occupant hydration metric based on a number of occupants within the building and the number of toilet or urinal flushes.

Another implementation of the present disclosure is one or more memory devices storing instructions thereon that, when executed by one or more processors, cause the one or more processors to receive water usage data from one or more network connected water valves, the water usage data indicating water usage by one or more occupants within the building, derive one or more health metrics indicating physical health of the one or more occupants based on the water usage data, and cause one or more pieces of building equipment to perform one or more operations based on values of the one or more health metrics, the one or more operations improving the physical health of the one or more occupants.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Overview

Figure 1:
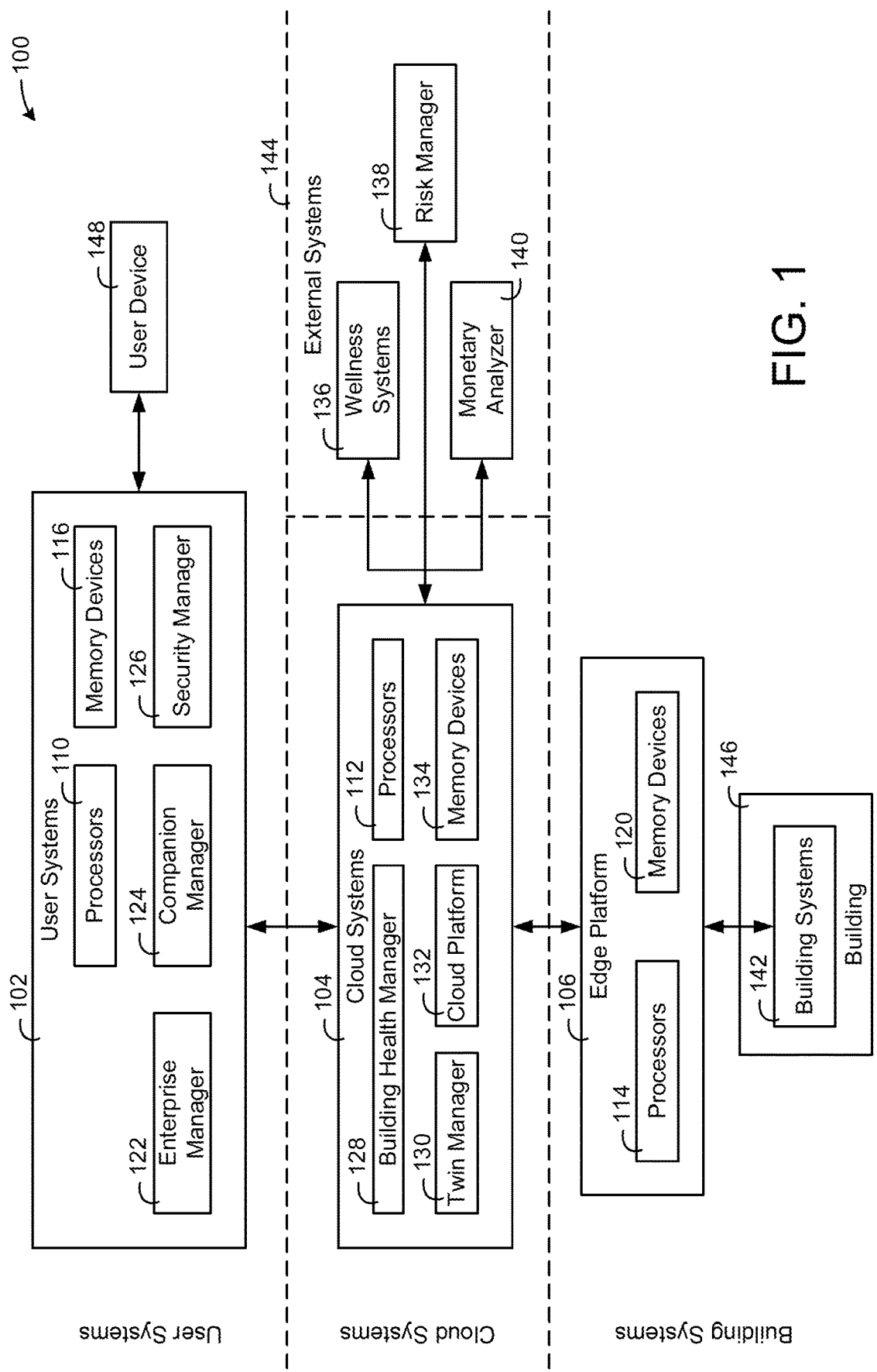
FIG. 1 is a block diagram of a system including building systems, cloud systems, and user systems including a building health manager for managing building health, according to an exemplary embodiment.

Referring generally to the FIGURES, systems and methods are shown for generating occupant health data based on information collected from connected water valves, according to an exemplary embodiment. The occupant health data can indicate information such as the physical health of an occupant, a level of infectious disease risk for the occupant, an indication of whether the occupant poses a threat to other occupants, etc. In some embodiments, connected water valves in a building may be installed throughout a building and collect water usage data, e.g., whether, and/or how much, water was consumed by a building appliance (e.g., toilet, urinal, bathroom sink, kitchen sink, water drinking fountain, etc.). In some embodiments, the connected water valves may communicate the water usage data to a building system via a network.

For example, the connected water valves may be installed in bathroom sinks, bathroom urinals, bathroom toilets, water drinking fountains, kitchen sinks, emergency eye wash systems, etc. The connected water valves may collect data indicating whether a urinal or toilet was flushed, whether an occupant washed their hands at a bathroom sink, whether an occupant drank water at a water drinking fountain, etc. This collected water usage data can be used to derive occupant health related information for particular occupants and/or particular spaces.

In some embodiments, the occupant health information could be hydration information. The hydration information could indicate an amount of water drank by an occupant and/or a group of occupants. For example, the number of toilet and/or urinal flushes could indicate the frequency at which occupants are using the bathroom in a building space. Based on a number of occupants of the building space and the number of flushes, the building system could determine a hydration level for an occupant and/or a group of occupants. The hydration level could indicate a number of toilet flushes per occupant per time period (e.g., hour, day, week). Furthermore, the hydration levels could be based on the amount of water usage at a water drinking fountain of the building space.

Furthermore, the occupant health information could indicate cleanliness of occupants with respect to washing their hands. For example, cleanliness levels for an occupant and/or group of occupants could be generated from the ratio of toilet flushes to sink runs to determine whether an occupant and/or occupants are washing their hands. For example, if a connected water valve for a urinal detects a flush but there is no subsequent connected valve detection of a sink running in the bathroom, an occupant may not have washed their hands. Furthermore, for a group of occupants, if the number of toilet flushes is significantly greater (e.g., a particular amount greater) than the number of sink runs, the building system may determine that occupants of the building may not be washing their hands after using the bathroom.

In some embodiments, the occupant health data can be generated by a building system for individual occupants, groups of occupants, or for building spaces. For example, the building system could determine occupant cleanliness or hydration levels for various floors of a building to determine which floors are performing well and which floors may need improvement. The building system can generate health profiles for individual occupants for the individual occupants to review via a user interface and/or building or building space profiles for building managers to review via a user interface. The feedback of the occupant health data can help encourage occupants to improve their behaviors or help building managers implement building control of equipment of a building.

Referring now to FIG. 1, a system 100 including building systems, cloud systems, and user systems including a building health manager for managing building health, according to an exemplary embodiment. The system 100 includes an edge platform 106, cloud systems 104, user systems 102, and/or external systems 144 (e.g., wellness systems 136, monetary analyzer 140, and/or a risk manager 138). The edge platform 106, the cloud systems 104, and/or the user systems 102 include processors 110-114 and/or memory devices 116-120.

The processors 110-114 and/or memory devices 116-120 can be devices of one or multiple servers, computer systems, cloud systems, etc. The processors 110-114 can be general purpose or specific purpose processors, application specific integrated circuits (ASICs), one or more field programmable gate arrays (FPGAs), a group of processing components, and/or other suitable processing component. The processors 110-114 may be configured to execute computer code and/or instructions stored in the memory devices 116-120 or received from other computer readable media (e.g., CDROM, network storage, a remote server, etc.).

The memory devices 116-120 can include one or more devices (e.g., memory units, memory devices, storage devices, etc.) for storing data and/or computer code for completing and/or facilitating the various processes described in the present disclosure. The memory devices 116-120 can include random access memory (RAM), read-only memory (ROM), hard drive storage, temporary storage, non-volatile memory, flash memory, optical memory, or any other suitable memory for storing software objects and/or computer instructions. The memory devices 116-120 can include database components, object code components, script components, or any other type of information structure for supporting the various activities and information structures described in the present disclosure. The memory devices 116-120 can be communicably connected to the processors 110-114 and can include computer code for executing (e.g., by the processors) one or more of the processors 110-114 described herein.

The cloud systems 104 includes a twin manager 130 and a cloud platform 132. The twin manager 130, the cloud platform 132, and/or the edge platform 106 can be the same as, or similar to, the components described U.S. patent application Ser. No. 17/134,671 filed Dec. 28, 2020, the entirety of which is incorporated by reference herein. The cloud systems 104 further include a building health manager 128. The edge platform 106 can be configured to integrate with building systems 142 to receive building data and provide the building data to the cloud systems 104. Furthermore, the cloud platform 132 can facilitate routing of the building data and/or enrichment of the building data based on a digital twin of a building managed by the twin manager 130. In some embodiments, the building systems 142 are environmental control systems, lighting systems, security systems, fire response systems, and/or any other type of building system.

The building health manager 128 can be configured to generate health scores for parameters such as planet health parameters, people health parameters, and/or space health parameters. Furthermore, the building health manager 128 can be configured to generate an overall health score from the scores for the planet health parameters, people health parameters, and/or space health parameters. The building health manager 128 can receive data from the building systems 142 and generate the scores for the planet health parameters, people health parameters, and/or space health parameters. The building health manager 128 can generate a building automation system (BAS) performance index, a light management system (LMS) performance index, a shade performance index, etc.

The building health manager 128 can receive building data from the building systems 142 and/or the external systems 144 for determining person health scores. The building data can include temperature, humidity, indoor air quality (IAQ), building lighting information, building sunshade information, seating information, sanitization information, emergency information, dining options, social distancing information, thermal control data, occupancy data, mental health data, social event data, etc. The building health manager 128 can determine occupant health scores for occupants and/or perform one or more control operations to improve the person health scores. For example, the building health manager 128 can determine and/or update control values for temperature, humidity, IAQ, light, and/or sunshade to improve person health scores.

The building health manager 128 can generate scores for system health of a building 146. The system health scores for building management systems (BMS), light management systems (LMS), sunshade systems, electrical metering and fire alarm systems, accessibility, transportation systems, parking management systems, power generation, access control systems, recycling systems, etc. Furthermore, the building health manager 128 can generate safety and security system health scores based on hardware point data, cyber security data (e.g., network cyber security data, Wi-Fi security data, firewall and/or port blocking data, antivirus data, etc.), fire alarm and suppression system data, electrical system data, water leak detection data, fire suppression system data, sprinkler system data, smoke detection data, staircase pressurization system data, evacuation system data, etc. Furthermore, the building health manager 128 can determine resource health scores for electrical usage, gas usage, and/or water usage (e.g., chilled or heated water usage) based on meter data received from the building systems 142.

The building health manager 128 can receive security system data from CCTVs, intrusion systems, glass-break systems, number plate recognition systems, evacuation system data, facial recognition systems, biometric reader systems. Furthermore, the building health manager 128 can be configured to generate service health scores indicating mechanical, electrical, sound systems, chemical systems, life safety, and transportation system, and/or plumbing system service.

In some embodiments, the building data received from the edge platform 106 is ingested and stored in a digital twin of the building 146 managed by the twin manager 130. The digital twin can be the digital twin described in U.S. patent application Ser. No. 17/134,671 filed Dec. 28, 2020. The digital twin can be a graph including edges and nodes representing the entities of the building 146 (e.g., the building 146, spaces of the building 146, devices, users, systems, etc.) and relationships between the entities. In some embodiments, the digital twin can store health data of the building 146 used by the building health manager 128 to generate the planet health scores, space health scores, people health scores, and/or overall building scores. The digital twin can store health related metadata descriptions for points, devices, systems, equipment, spaces, buildings, etc. The digital twin can, in some embodiments, store health scores for the entities of the digital twin, e.g., health scores for buildings, spaces, people, etc.

In some embodiments, the building health manager 128 can be configured to search and filter health criteria for displaying health information and scores on a user device 148. Furthermore, various building control operations, e.g., calculations, logic, workflows, automation, machine learning, artificial intelligence, etc. that the building health manager 128 may execute to control the building systems 142, can all incorporate health scores for inputs and outputs of the building control operations. In this regard, the building control operations may execute to account for health and improve health scores. For example, a machine learning algorithm that determines setpoints to use in a zone based on predicted occupancy can incorporate health scores into the setpoint optimization to determine setpoints that result in ideal health scores.

The cloud systems 104 are configured to receive health data from the various external systems 144. The health data received from the external systems 144 can be used by the building health manager 128 to determine health scores. For example, the cloud systems 104 can connect with other external systems 144 managed and/or owned by the same or a different entity, e.g., partner systems. The wellness systems 136 can provide information on the mental, emotional, and/or physical health of occupants of the building 146. The risk manager 138 can provide risk related data for the building 146, the building systems 142 of the building 146 and/or occupants of the building 146. For example, the risk manager 138 can provide risk scores to the cloud systems 104. The risk manager 138 can be the systems described in U.S. application Ser. No. 16/143,221 filed Sep. 26, 2018, the entirety of which is incorporated by reference herein. The external systems 144 further include a monetary analyzer 140. The monetary analyzer 140 can be configured to perform monetization optimizations and/or provide expense reports of the building 146 to the cloud systems 104 based on the operation of the building systems 142.

The system 100 includes a user device 148. The user device 148 can be any device that provides information to a user and receives input from the user. The user device can include various input and/or output devices, e.g., a keyboard, a mouse, a touch screen, a microphone, a speaker, a display, etc. The user device 148 can be a smartphone, a tablet, a laptop, a desktop computer, a console, a smart television, etc.

The user systems 102 can manage user interfaces displayed on the user device 148. The user systems 102 can generate the user interfaces and cause the user device 148 to display the user interfaces. In some embodiments, the user systems 102 can be configured to provide input to the user systems 102 via the user interfaces. The user systems 102 include an enterprise manager 122, a companion manager 124, and a security manager 126. The user interfaces may be the user interfaces shown and described with reference to FIGS. 13-18, 37, and 38.

The enterprise manager 122 can generate one or more interfaces that provide visibility to building health aspects with health scores, descriptions, trends, insights, and/or actionable recommendations. The enterprise manager 122 can provide easy, intuitive navigation and drill down for rollups of health data to organize detailed information related to concepts and scores. Furthermore, the interfaces can include progress reports.

The companion manager 124 can provide occupant health information in user interfaces. The occupant health information can include feedback on clean, comfortable spaces (e.g., air, water, light, sanitization, etc.), social distancing and connectivity information, productivity measures, nourishment and fitness goals, reward points, etc. Furthermore, the companion manager 124 can provide user interfaces including health information for spaces. The information can include systems availability and/or provide feedback on janitorial services. Furthermore, the companion manager 124 can provide planet health information. For example, the interface can include responsibility and conversation information, corporate sustainability progress and success, nature information, and/or reward points.

The security manager 126 can provide security information via user interfaces for security professionals. The information can include health for spaces (e.g., places within a building), safety and security risk information, process and actionable recommendations for improving health and/or risk, etc.

In some embodiments, the cloud systems 104 can receive data from the building systems 142 and/or the external systems 144. The building health manager 128 can generate health scores based on the data. The data can include space equipment relationships, time series data for temperature, humidity, pressure, IAQ, velocity, light and sunshade data. In some embodiments, the building health manager 128 can be configured to generate thermal, air, and/or light health scores based on the data. Furthermore, based on the data, the health manager 128 can perform HVAC, light, and/or sunshade command and/or control. In some embodiments, the cloud systems 104 can manage a pest administration portal to review and schedule pest control for the building 146.

In some embodiments, the building health manager 128 can be configured to receive mechanical and/or electrical fault data from the building systems 142. Based on the fault data (or the absence of fault data), the building health manager 128 can generate building health scores for the building 146. The fault data can include high air pressure faults, high water pressure faults, high temperature faults, coil freezing faults, high voltage faults, overload faults, short circuit faults, earth faults, high harmonic faults, etc.

Figure 2:
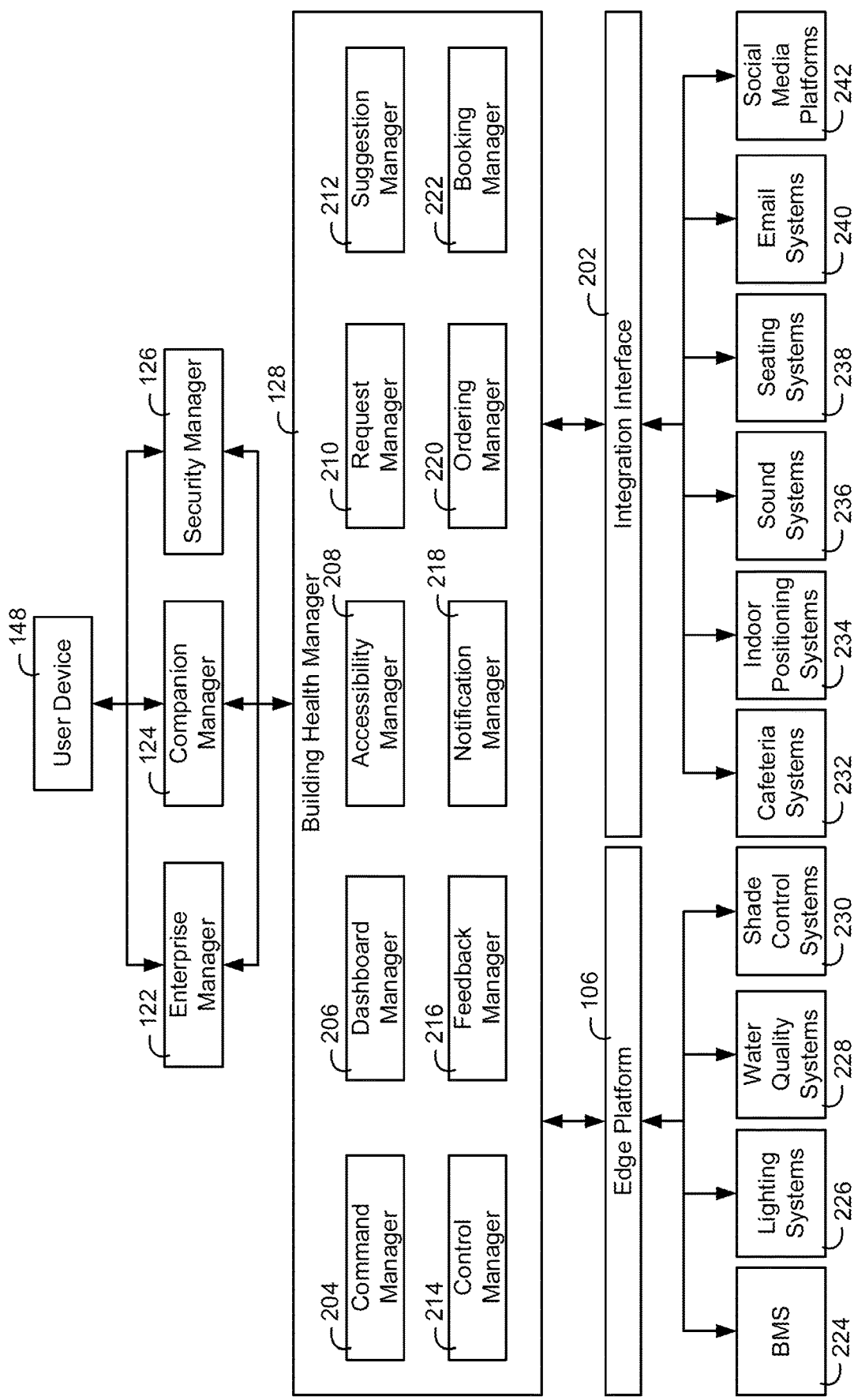
FIG. 2 is a block diagram of the building health manager in greater detail, according to an exemplary embodiment.

Referring now to FIG. 2, the building health manager 128 is shown in greater detail, according to an exemplary embodiment. The building health manager 128 is shown to receive building data from systems 224-242 via the edge platform 106 and via an integration interface 202. The systems 224-242 can be systems of the building systems 142. In some embodiments, the integration interface 202 is an Application Programming Interface (API) that interfaces systems 234-242 with the building health manager 128. The building management system (BMS) 224 which can include systems for heating the building 146, cooling the building 146, controlling air quality within the building 146, etc. The lighting systems 226 can include lights and/or light control systems configured to control lighting parameters in various zones of the building 146, e.g., turn lights on or off, control the level of light, control the hue of light, etc.

The water quality systems 228 can be configured to measure water quality of water for the building 146, e.g., water used in the building 146 or used by particular systems of the building 146. The shade control system 230 can be configured to control the shades (e.g., control shade position) of various windows of the building 146. The cafeteria systems 232 can be configured to manage food ordering and/or food delivery within the building 146. The indoor positioning systems 234 can be configured to identify occupants and/or track the location of occupants within the building 146, e.g., through Wi-Fi triangulation or trilateration, Bluetooth beacons, 5G tracking, GPS, etc.

The sound systems 236 can be control sound played by speakers throughout various zones of the building 146. The sound systems 236 can control announcements, music, white noise, etc. The email systems 240 can manage email servers for sending and/or receiving emails. The email systems 240 can manage email accounts for various employees, tenants, and/or users of the building 146. The social media platforms 242 can be a social media platform that facilitates message post feeds, group conversations, messaging, etc. The social media platforms 242 can include social media accounts for the building 146 or entity, e.g., a company, a tenant of the building 146, an employee of the building 146, etc.

The seating systems 238 can be systems that perform desk scheduling, e.g., hot desking. Furthermore, the seating systems 238 can track the number and locations of desks, seats, tables, chairs, couches, etc. throughout the building. For example, the seating systems 238 can provide the building health manager 128 with data pertaining to seating, seating scheduling, and/or what types of seats occupants are using.

The building health manager 128 includes various components for managing or operating the systems 224-242. The building health manager 128 includes a command manager 204, a dashboard manager 206, an accessibility manager 208, a request manager 210, a suggestion manager 212, a control manager 214, a feedback manager 216, a notification manager 218, an ordering manager 220, and a booking manager 222.

The command manager 204 can be configured to control systems 224-242. The command manager 204 can receive commands for controlling characteristics of the building 146 from the user device 148 and operate the systems 224-242 based on the commands. The command manager 204 can control zone temperature, control HVAC equipment on or off status, control optimum equipment start, control humidity, control indoor air quality (IAQ), control static pressure, operate an air/night purge mode, control air velocity in the building 146, control particulate matters in the building 146, activate filters, control organic gasses in the building 146, control inorganic gasses in the building 146, control radon levels in the building 146, control water quality in the building 146, control water temperature, turn lights on or off, control light intensity, control sunshades, control noise levels of the building 146, control music played in the building 146, personalize comfort, turn desk lights on or off, control desk light intensity, control desk light color, control music played in a gym, etc.

The dashboard manager 206 can generate dashboards for display via the user device 148. The user device 148 can provide input via the dashboards. The dashboard can display, and/or provide control over, zone temperature, static pressure, air velocity, particulate matters, gasses, water quality, light status, sunshade status, sanitization status, gym occupancy status, etc.

The feedback manager 216 can aggregate feedback received from the user device 148. The feedback manager 216 can generate feedback reports based on the feedback collected. The feedback reports can include complaints and/or feedback over building smell, water quality, noise levels, employee sickness, etc.

The accessibility manager 208 can facilitate navigation or directions for the user device 148. The accessibility manager 208 can receive navigation requests via the user device 148 and generate navigation directions for display to the user via the user device 148. The navigation directions can aid users in finding or viewing information pertaining to water refilling stations, eating areas, contract tracing, gardens, other employees, rooms, etc. In some embodiments, the accessibility manager 208 receives data from elevator systems and/or escalator systems.

The notification manager 218 can be configured to generate alerts pushed and/or communicated to the user device 148. The alerts can be a dehydration alert, a sunshade alert, a sanitization completed alert, duress alarms, a food order ready alert, a fruit basket arrived alert, a lunch break alert, a coffee break alert, an eye relaxation alert, a social distancing alert, a health data alert, a fitness program alert, a pest control status, a fitness awareness alert, a no movement alert, a gym occupancy alert, a hand washing alert, a sanitization alert, a medical emergency alert, an indoor air quality alert, a bush fire alert, a mental health program alert, a nearby social event alert, etc.

The request manager 210 can receive requests from the user device 148 and make control updates and/or notify technicians to improve systems of the building 146 based on the requests. The requests may be requests to improve smell, improve air replacement, add more water refilling stations, request a desk or room booking, request sanitization for an area or desk, order food, pest control, playing music in a gym, facilitate air replacement, book a bicycle or vehicle, etc.

The ordering manager 220 can be configured to order food and/or drinks for users. A user can place an order to the cafeteria systems 232 via the user device 148. In some embodiments, the order can include a delivery request with delivery location (e.g., employee desk).

The suggestion manager 212 can be configured to generate suggestions for improving employee mental and/or physical health. The suggestion manager 212 can send the suggestions to the user device 148. The suggestions may be nourishment education, physical activity suggestions, hand washing suggestions, mental health suggestions, suicide prevention help, etc. The booking manager 222 can be configured to facilitate room or desk booking. For example, the booking manager 222 can book conference rooms, meeting rooms, make gym appointment bookings, etc. Furthermore, the booking manager 222 can facilitate desk booking, e.g., hot-desking.

Figure 3:
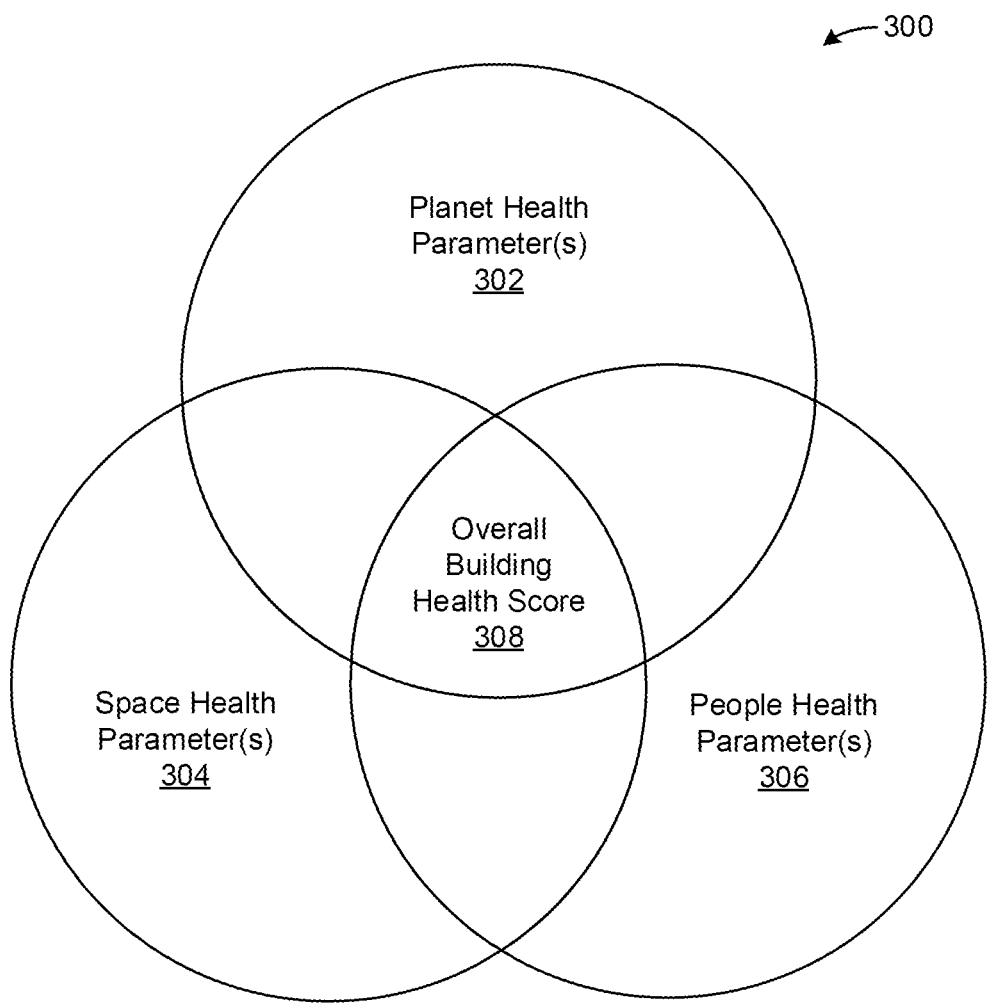
FIG. 3 is a Venn diagram of planet health parameters, space health parameters, and people health parameters contributing to an overall building health score, according to an exemplary embodiment.

Referring now to FIG. 3, a Venn diagram 300 of planet health parameters 302, space health parameters 304, and people health parameters 306 contributing to an overall building health score 308 is shown, according to an exemplary embodiment. The planet health parameters 302, the space health parameters 304, and the people health parameters 306 can individually describe the health of different aspects of the building 146, e.g., the planet, spaces of the building 146, and people of the building 146. Together, the planet health parameters 302, the space health parameters 304, and the people health parameters 306 can contribute to an overall building health score 308. In some embodiments, the people health parameters 306 do not include any medical records of individuals. In this regard, the building health manager 128 can determine the influence of building system operation on the mental and/or physical health of occupants without requiring private medical records.

The planet health parameters 302 can be scores that describe the effect of operating the building 146 on the planet. For example, the planet health parameters 302 can indicate how much energy is consumed by the building 146, how much pollution is generated by the building 146, how much air is filtered by the building 146, etc.

The people health parameters 306 can be scores that describe the effect of operation of the building 146 and/or services offered by the building 146 on people, occupants of the building 146. The people health parameters 306 can indicate mental and/or physical health of occupants of the building 146. For example, temperature and/or humidity settings can be rated according to occupant comfort. Light levels, light color, and/or light hue can be rated according to the mental affect that the light has on the occupants. Similarly, services such as having a gym, personal trainer, healthy food options, etc. offered by the building 146 can indicate whether the scores describing whether the occupant health is high or low.

The space health parameters 304 can indicate the health levels of spaces of the building 146. For example, the presence of faults in building environmental control systems can indicate whether the building environmental control systems are operating well. Furthermore, emergencies such as flooding, fire, cyber security attacks, etc. can all indicate the health of space of the building 146.

Figure 4:
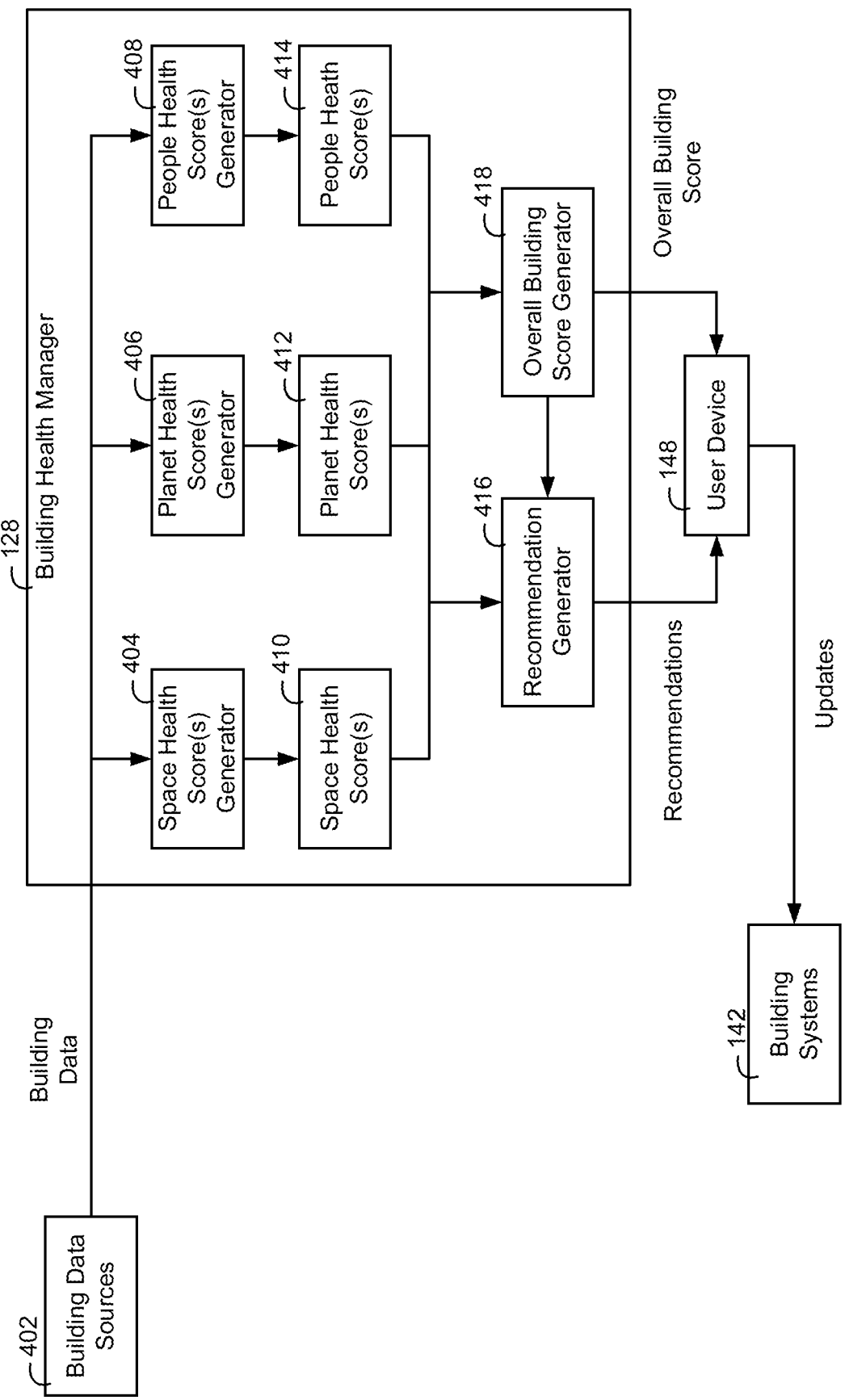
FIG. 4 is a block diagram of the building health manager generating an overall building score from space health scores, planet health scores, and people health scores, according to an exemplary embodiment.

Referring now to FIG. 4, the building health manager 128 is shown generating an overall building score from space health scores, planet health scores, and people health scores, according to an exemplary embodiment. The building health manager 128 can receive building data from building data sources 402. For example, the building data sources 402 can include local subsystems of the building 146 operating at the building, e.g., the building systems 142. Furthermore, the building data sources 402 can include the external systems 144. The building data received by the building health manager 128 can include data such as space temperature, humidity, light levels, equipment fault data, water usage, occupant locations, meeting productivity, food or drink menu nutrition levels, occupant physical activity levels, and/or any other data described herein.

The building health manager 128 includes a space health scores generator 404, a planet health scores generator 406, and a people health scores generator 408. The space health scores generator 404 can generate space health scores 410 for the space health parameters 304. The planet health scores generator 406 can generate the planet health scores 412 for the planet health parameters 302. The people health scores generator 408 can generate people health scores 414 for the people health parameters 306. In some embodiments, the scores generated by the space health scores generator 404, the planet health scores generator 406, and the people health scores generator 408.

For example, for the people health scores 414, the people health scores generator 408 can generate scores for parameters that indicate whether a workplace is safe and secure, whether a work environment is comfortable, enhanced productivity of a space, stress of occupants, nutrition and exercise of occupants, frictionless access and services offered by the building 146, social distancing and contact tracing of the building 146, and hand washing of the building space.

For example, the people health scores generator 408 could generate scores for each parameter. For example, the people health score generator 408 can generate a score of 9 for the workplace safety and security parameter, a score of 8 for the work environment comfortability parameter, a score of 7 for an enhanced productivity of a space parameter, a score of 7 for a stress of occupants parameter, a score of 8 for a nutrition and exercise of occupants parameter, a score of 10 for a frictionless movement parameter, a score of 6 for a social distancing parameter, a score of 9 for a contact tracing parameter, and a score of 7 for a hand washing parameter. Based on the scores for the parameters, the people health scores generator 408 can generate a people health score, e.g., with a score of 8. Similar determinations can be generated for the space health scores 410 by the space health scores generator 404 and the planet health scores 412 by the planet health scores generator 406.

Based on the space health scores 410, the planet health score 412, and/or the people health scores 414, the building health manager 128 can be configured to generate an overall building score with the overall building score generator 418 of the building health manager 128. The overall building score generator 418 can generate an average (e.g., a weighted average) of the space health scores 410, the planet health scores 412, and/or the people health scores 414. The overall building score generator 418 can be configure to provide the overall building score to a recommendation generator 416 and/or the user device 148 via a user interface (e.g., the user interfaces shown and described with reference to FIGS. 9 and 10).

The recommendation generator 416 can generate recommendations for improving the overall building score, the space health scores 410, the planet health scores 412, and/or the people health scores 414. The recommendation generator 516 can generate recommendations to update temperature of spaces, update lighting levels of spaces, offer healthier cafeteria food, offer workout classes, reduce employee workload, improve occupant social distancing, etc.

In some embodiments, the recommendations can be specific to the space health scores 410, the planet health scores 412, and/or the people health scores 414. For example, the recommendations could be specific to the people health scores 414. For example, the recommendation could be to condition meeting rooms prior to a meeting to ensure occupants are comfortable from the start, increase light levels in the building 146 due to lack of natural light, add a wayfinding service to the building 146 to help occupants efficiently navigate the building, remind occupants of proper hand washing techniques, etc.

The recommendations can be provided to a user via the user device 148 by the recommendation generator 416. The user device 148 can approve the recommendations and make updates to the building systems 142, e.g., the building health manager 128 can provide setting updates to the building systems 142 updating the operation of the building systems 142 in response to receiving user approval. In some embodiments, the building health manager 128 can generate work orders. For example, the work orders may be work orders to install new equipment or services, perform maintenance, etc. Furthermore, in some embodiments, the building health manager 128 can implement the recommendations automatically without requiring user approval.

Figure 5:
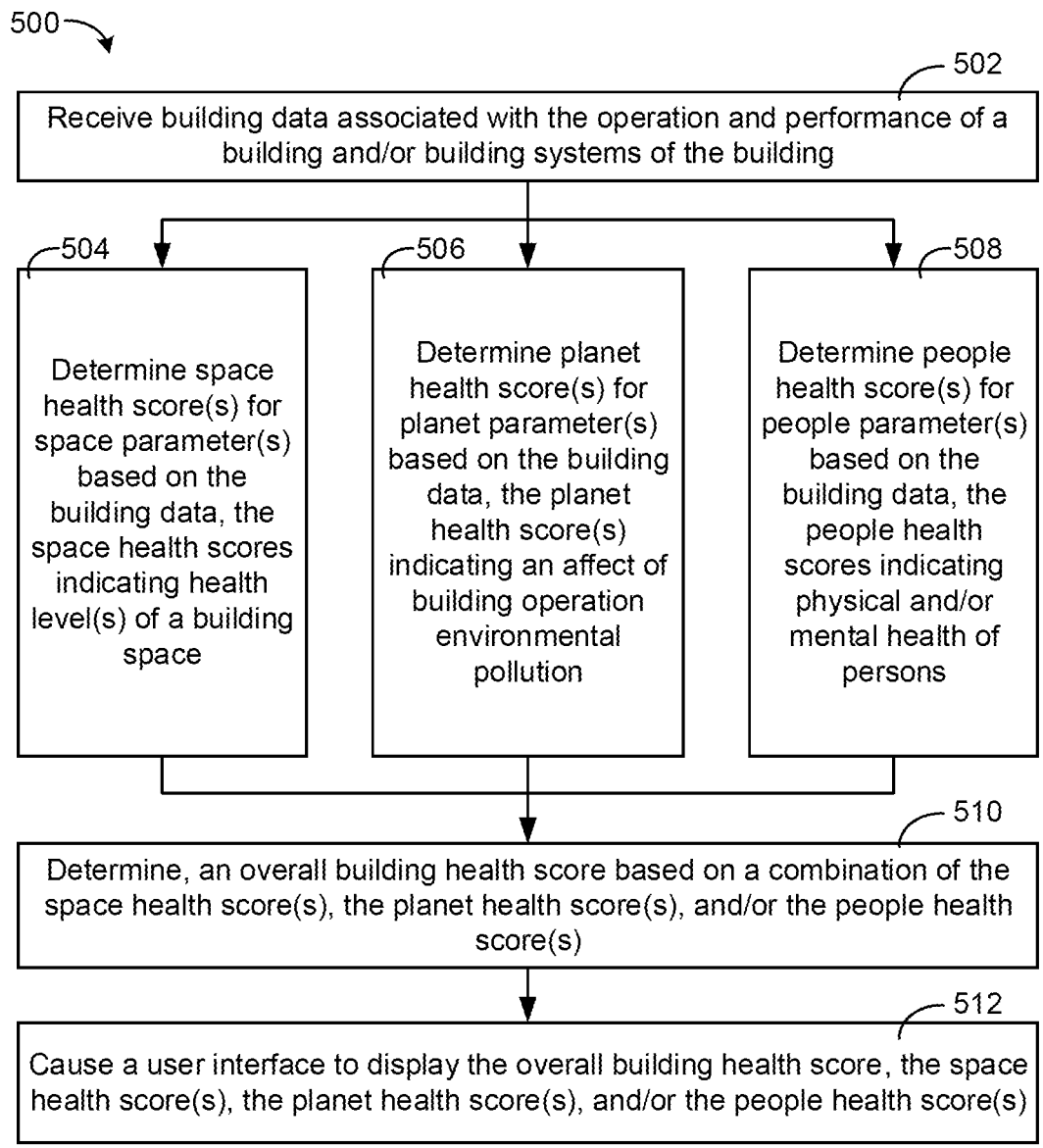
FIG. 5 is a flow diagram of a process of generating the overall building score from the space health scores, the planet health scores, and the people health scores, according to an exemplary embodiment.

Referring now to FIG. 5, a flow diagram of a process 500 of generating the overall building score from the space health scores 510, the planet health scores 512, and the people health scores 514 is shown, according to an exemplary embodiment. The building health manager 128 can be configured to perform the process 500. Furthermore, any computing system or device described herein can be configured to perform the process 500.

In step 502, the building health manager 128 can receive building data associated with the operation and performance of the building 146 and/or the building systems 142. The building health manager 128 can receive operational data of the building systems 142, identifying information identifying what subsystems are present in the building 146, data from the external systems 144, etc.

In step 504, the building health manager 128 can determine the space health scores 510 for the space health parameters 304 based on the building data. For example, the building health manager 128 could determine a score for each of the space health parameters 304. In some embodiments, the building health manager 128 can generate a composite space health score based on the scores for each of the space health parameters 304.

In step 506, the building health manager 128 can determine the planet health scores 512 for the planet health parameters 302 based on the building data. For example, the building health manager 128 could determine a score for each of the planet health parameters 302. In some embodiments, the building health manager 128 can generate a composite planet health score based on the scores for each of the planet health parameters 302.

In step 508, the building health manager 128 can determine the people health scores 514 for the people health parameters 306 based on the building data. For example, the building health manager 128 could determine a score for each of the people health parameters 306. In some embodiments, the building health manager 128 can generate a composite people health score based on the scores for each of the people health parameters 306.

In step 510, the building health manager 128 can be configured to generate an overall building health score based on a combination of the space health scores 510, the planet health scores 512, and the people health scores 514. For example, the building health manager 128 can generate an average of the space health scores 510, the planet health scores 512, and the people health scores 514. In some embodiments, the average is a weight average. In some embodiments, a user provides weight values for weighting each of the space health scores 510, the planet health scores 512, and the people health scores 514.

In step 512, the building health manager 128 can cause a user interface to display the overall building health score determined in the step 510. In some embodiments, the building health manager 128 causes the user interface to include the space health scores 510, the planet health scores 512, and the people health scores 514. The building health manager 128 can cause the user device 148 to display the user interface.

Figure 6:
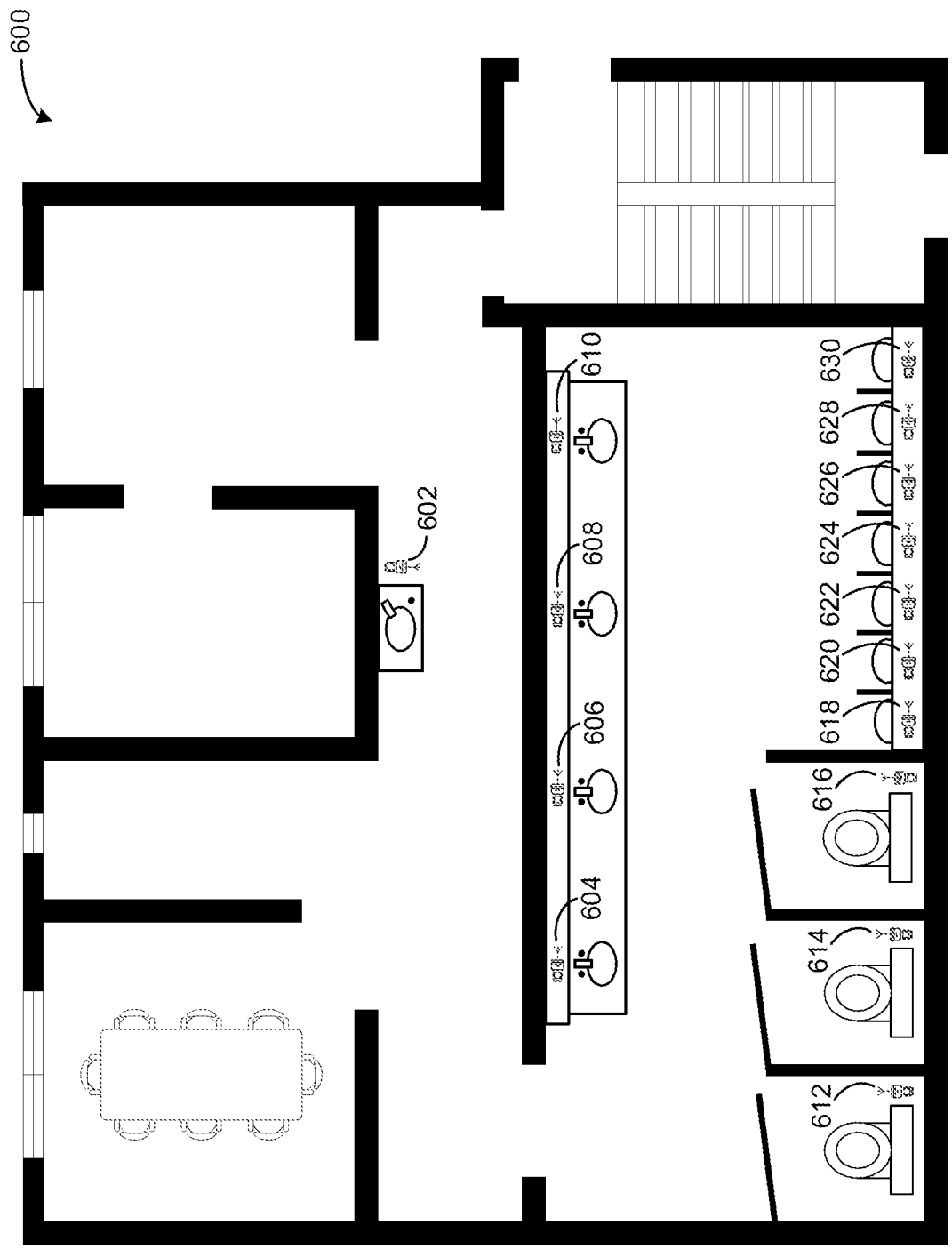
FIG. 6 is a schematic diagram of a floor of a building including connected water valves in toilets, sinks, and water fountains of a floor of a building, according to an exemplary embodiment.

Referring now to FIG. 6, a schematic diagram 600 of a floor of a building including connected water valves 602-630 in toilets, sinks, and water fountains of a floor of a building is shown, according to an exemplary embodiment. The floor of FIG. 6 may be a floor of the building 146. The connected water valves 602-630 can be connected to the building health manager 128 via the edge platform 106 and/or the integration interface 202 via one or more wired and/or wireless networks (e.g., Wi-Fi, Bluetooth, Ethernet, RS-485, etc.). The connected water valves 602-630 can provide data indicating the time of a water valve actuation, an amount of water used by the water valve actuation, a flow rate of the water, etc.

The connected water valve 602 may be installed in a water drinking fountain that occupants of the floor of FIG. 6 drink water from. The connected water valve 602 can record each time an occupant causes the water drinking fountain to turn on and provide water. The connected water valve 602 can further record the amount of water provided each time the water drinking fountain is turned on.

The connected water valves 604-610 can be installed in sinks of a bathroom. In some embodiments, the connected water valves 604-610 are installed in sinks of a surgery preparation room, a laboratory, a kitchen, etc. The connected water valves 604-610 can collect data indicate a time at which the sink is run by an occupant washing their hands, the length of time that the occupant washes their hands, etc.

The connected water valves 612-616 can be installed in toilets of a bathroom. The connected water valves 612-616 can record data indicating that a toilet was flushed, the time the toilet was flushed, and the amount of water used in each flush. Similarly, the connected water valves 618-630 can be installed in urinals of the bathroom. The connected water valves 618-630 can record data indicating that the urinal was flushed, the time the urinal was flushed, and the amount of water used in each flush.

Figure 7:
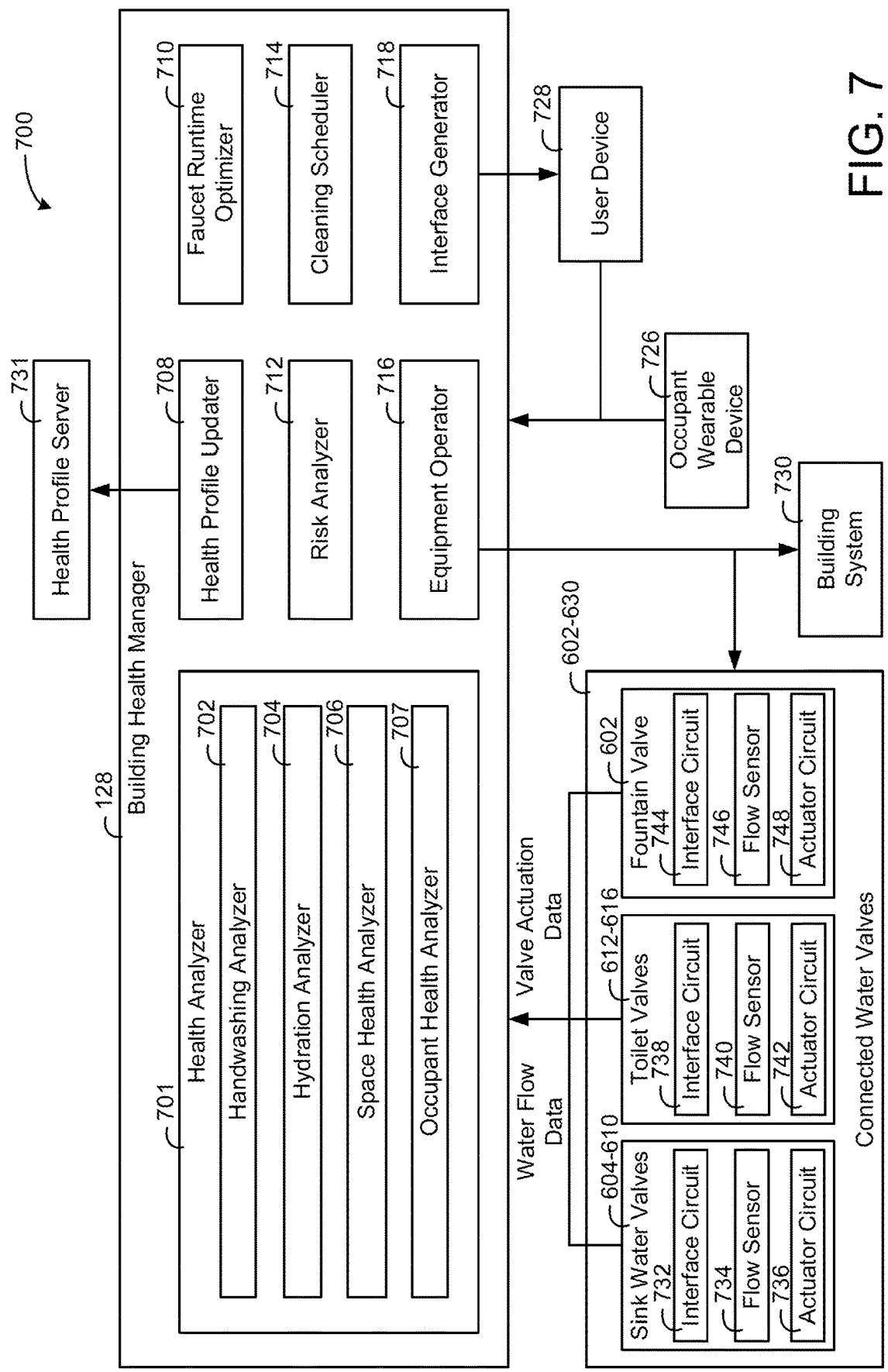
FIG. 7 is a block diagram of the building health manager of FIG. 4 receiving valve data from the connected water valves of FIG. 6 where the building health manager generates occupant health data based on the valve data, according to an exemplary embodiment.

Referring now to FIG. 7, a system 700 of the building health manager 128 receiving valve data from the connected water valves 602-630 of FIG. 6 where the building health manager 128 generates occupant health data based on the valve data, according to an exemplary embodiment. The building health manager 128 receives water flow indication, e.g., how much water was consumed by each of the connected water valves 602-630 during a flush or running water, a flow rate during each flush or when water is running, etc. The connected water valves 602-630 can further provide one or more timestamps for each water consumption amount or flow rate. Furthermore, the building health manager 128 receives valve actuation data indicating an actuator of the valve, e.g., opening, closing, providing water flow, providing a water flush, ending a water flow, ending a water flush, etc. The actuator events may be associated with a timestamp provided by the connected water valves 602-630.

The connected water valves 602-630 can include interface circuits 732, 738, and 744. The interface circuits 732, 738, and 744 can facilitate communication with the edge platform 106, integration interface 202, the cloud systems 104, the building health manager 128, etc. For example, the interface circuits 732, 738, and 744 can include wired and/or wireless transceivers, radios, etc. for facilitating network communication via a Wide Area Network (WAN), a Local Area Network (LAN), the Internet, Wi-Fi, Bluetooth, Zigbee, etc. The interface circuit 732 can communicate the water flow data and/or the valve actuation data to the building health manager 128. Furthermore, the building health manager 128 can communicate control commands to the connected water valves 602-630 to implement control of the connected water valves (e.g., control flush lengths, control water faucet run times, etc.).

The connected water valves 602-630 include flow sensors 734, 740, and 746. The flow sensors 734, 740, and 746 can be configured to measure flow rates of water. For example, the flow sensors 734, 740, and 746 can be configured to measure a flow rate and/or a water consumption amount for toilets, sinks, urinals, etc. The interface circuits 732, 738, and 744 can communicate the measurements and/or measurement derivations of the flow sensors 734, 740, and 746 to the building health manager 128.

The connected water valves 602-630 include actuator circuits 736, 742, and 748. The actuator circuits 736, 742, and 748 can operate to open and/or close a valve to cause water to flow or to stop water from flowing. The actuator circuits 736, 742, and 748 can include buttons or motion sensors that detect whether or not to execute, e.g., whether or not a toilet should flush, whether or not a sink should run, etc.

The building health manager 128 includes a health analyzer 701 that is configured to analyze the water flow indications and/or the valve actuation data to determine occupant health data (e.g., occupant health analytics, metrics, and/or scores) for individual occupants, groups of occupants, buildings, and/or building spaces. The health analyzer 701 includes a handwashing analyzer 702, a hydration analyzer 704, and a space health analyzer 706.

The handwashing analyzer 702 can generate handwashing health data, e.g., cleanliness data, based on the water flow data and/or the valve actuation data. In some embodiments, the handwashing analyzer 702 can correlate toilet and urinal flushes with bathroom sink actuations. For example, the handwashing analyzer 702 can determine, for a period of time (e.g., a rolling window) a number of toilet flushes for a bathroom to a number of sink actuations for the bathroom. Ideally, the ratio should indicate that the number of toilet flushes is the same as, or less than, the number of sink actuations. Furthermore, the handwashing analyzer 702 can analyze valve actuation data and/or water flow data to indicate a length of time that a sink was run. For example, the handwashing analyzer 702 can compare a water run time to an ideal water runtime.

If the recorded water run time is equal to or greater than the ideal water run time, the handwashing analyzer 702 can identify that a handwashing event was done properly. If the recorded water run time is less than the ideal water run time, the handwashing analyzer 702 can identify that the handwashing event was not performed properly (e.g., the occupant did not wash their hands long enough). The handwashing analyzer 702 can track a percentage of proper handwashing to track the performance of handwashing in a bathroom, floor, and/or building space.

The health analyzer 701 includes a hydration analyzer 704. The hydration analyzer 704 can be configured to analyze hydration levels of occupants, groups of occupants, or occupants of certain building spaces or buildings. The hydration analyzer 704 can generate a hydration score indicating whether an occupant or occupants are consuming enough fluids during a time period. In some embodiments, the health analyzer 701 is configured to correlate the number of toilet and/or urinal flushes to hydration levels of a population. For example, the more frequently occupants use the bathroom (e.g., per occupancy level), this may indicate that the occupants are drinking more water and have higher hydration levels.

In some embodiments, the hydration score is based on a number of bathroom visits per occupant. For example, the hydration score may be a number of bathroom flushes of a space to number of occupants of the space (e.g., number of occupants detected in a building, number of occupants who work on a floor, etc.). For example, a total number of bathroom flushes can be compared to a number of occupants of the floor. This can indicate a hydration level for the floor.

In some embodiments, the health analyzer 701 can communicate with an occupancy tracking system that identifies occupancy level for various spaces (e.g., buildings, floors of buildings, zones of buildings, rooms of buildings, etc.) based on occupancy sensors. The occupancy sensors may, in some embodiments, be motion sensors (e.g., passive infrared sensors (PIRs), a system aggregating geolocation collected by Global Positioning Systems (GPS) of user devices, through a system that correlates occupant work location in a building with access control system detections of occupants, Bluetooth beacon systems, etc. The health analyzer 701 can correlate the occupant levels with the water flow data and/or valve actuation data to identify flow data and/or valve actuation data on an occupant level (e.g., toilet flushes per occupant, fountain valve flow per occupant, etc.).

The space health analyzer 706 can be configured to track the handwashing scores of the handwashing analyzer 702 on a space by space level. Furthermore, the space health analyzer 706 can track the hydration scores on a space by space level. In some embodiments, the space health analyzer 706 tracks handwashing and/or hydration scores for certain building spaces, floors of a building, buildings within a campus, or buildings or campuses within an enterprise. In some embodiments, the space health analyzer 706 sorts water flow data and/or valve actuation data received form the connected water valves 602-630 based on location of the connected water valves 602-630 and calculates the handwashing scores and/or hydration scores (e.g., with the handwashing analyzer 702 and/or the hydration analyzer 704) for each sorted location.

The occupant health analyzer 707 is configured to track handwashing and/or hydration on an occupant by occupant level. In some embodiments, the occupant health analyzer 707 received occupant tracking data from the indoor positioning systems 234, from an occupant wearable device 726 (e.g., smartwatch, wireless identifier card, smart bracelet, smart jewelry, smart ring, etc.), and/or a user device 728 (e.g., cellphone, tablet, laptop, etc.). The occupant tracking data can indicate whether the occupant visited a bathroom, whether the occupant visited a bubbler, etc. The occupant health analyzer 707 can determine hydration and/or handwashing scores for an occupant.

In some embodiments, the occupant wearable device 726 and/or user device 728 communicates with the connected water valves 602-630. For example, the connected water valves 602-630 can be wireless beacons (e.g., Bluetooth) that communicate with the occupant wearable device 726 and/or the user device 728. Furthermore, the occupant wearable device 726 and/or the user device 728 can communicate with the connected water valves 602-630 and provide occupant identifying information. The occupant health analyzer 707 can analyze water flow data and/or valve actuation data that includes an occupant identifier indicating that a particular occupant flushed a toilet, flushed a urinal, washed their hands at a sink, drank from a bubbler etc. The occupant health analyzer 707 can be configured to determine, via the handwashing analyzer 702, if the occupant washes their hands after flushing a toilet, how much water the occupant drinks from a fountain, etc.

The building health manager 128 further includes a health profile updater 708. The health profile updater 708 can be configured to update a health profile for a user stored and managed by a health profile server 731. The health profile server 731 may store data indicating heart rate levels, sleep data, and/or any other information collected from the occupant wearable device 726. The health profile updater 708 can provide the hydration scores determined by the hydration analyzer 704 and/or the handwashing score determined by the handwashing analyzer 702. The health profile updater 708 can communicate with an endpoint of the health profile server 731 to provide the scores for particular occupants to the health profile server 731. When the user logins in, via their user device 728, to view health data of their health profile via the health profile server 731, the user can view the hydration and/or handwashing scores.

The faucet runtime optimizer 710 can be configured to optimize a runtime of a water faucet operated by the sink water valves 604-610. The faucet runtime optimizer 710 can be configured to identify a proper water faucet runtime. In some embodiments, the sink water valves 604-610 can be configured to actuate and run water for a set period of time responsive to receiving a button press or hand motion detection. The faucet runtime optimizer 710 can be configured to identify the set period of time for the sink water valves 604-610. The faucet runtime optimizer 710 can run an optimization of water cost and number of run requests to select a runtime that minimizes a number of sequential requests for water to run and minimizes water cost. The faucet runtime optimizer 710 can lengthen a sink runtime if occupants frequently request water to run to many times in a row. Furthermore, the faucet runtime optimizer 710 can identify the cost of water run and minimize the water costs to an ideal level, e.g., reducing the water runtime to a level that creates an acceptable number of sequential water run requests.

The building health manager 128 includes a risk analyzer 712. The risk analyzer 712 can be configured to generate infectious disease risk information for an occupant, a space, a building, etc. The risk analyzer 712 can generate the infectious disease risk score based on handwashing scores and/or hydration scores determined by the health analyzer 701. In some embodiments, a poorer handwashing level for a building can cause an infectious disease risk score for the building to increase since the transmission of the infectious disease may increase if occupants do not wash their hands or do not wash their hands properly. The risk analyzer 712 can be configured to perform risk scoring such as discussed in U.S. application Ser. No. 17/220,795 filed Apr. 1, 2021 and U.S. patent application Ser. No. 16/783,936 filed Feb. 6, 2020, the entirety of which are incorporated by referenced herein.

The building health manager 128 includes a cleaning scheduler 714. The cleaning scheduler 714 can be configured to schedule cleaning in various areas of the building. For example, the cleaning scheduler 714 can schedule cleaning for an area of a building based on the space health analyzer 706. For example, if cleanliness levels of a building floor are low, e.g., a ratio of toilet and urinal flush events to occupant handwashing events is greater than a particular level, the cleaning scheduler 714 can determine that the floor needs cleaning. In some embodiments, a value of the ratio can be used to schedule a level of cleaning for the floor. For example, various ranges of the ratio can correlate to various cleaning depths. For example, for a ratio of 1 to 1.5, a first level of cleaning can be scheduled by the cleaning scheduler 714, for a ratio of 1.6 to 2, a second level of cleaning can be scheduled by the cleaning scheduler 714, etc.

In some embodiments, the cleaning scheduler 714 can schedule cleaning for the floor by generating a cleaning work order and providing the cleaning work order to a user device of cleaning personal, e.g., the user device 728. In some embodiments, the cleaning can be performed by the building system 730, e.g., robotic vacuums, flying drones that spray disinfection liquids and aerosols, ultraviolet cleaning lights installed in a building, etc. The cleaning scheduler 714 can cause the building system 730 to perform the cleaning, in some embodiments.

The building health manager 128 includes an equipment operator 716. The equipment operator 716 can be configured to operate the building system 730 to operate a building based on the handwashing score generated by the health analyzer 701 and/or the hydration scores generated by the occupant health analyzer 707. For example, if the handwashing scores for a space is below a particular level, the equipment operator 716 can operate one or more air handling units (AHUs) to increase air changes in the low performing space. Furthermore, if the faucet runtime optimizer 710 determines a runtime length for a sink water valve, the equipment operator 716 can push the runtime length to the connected water valves 602-630.

In some embodiments, the equipment operator 716 can identify faults based on water flow data or valve actuation data, e.g., broken valve, clogged drain, etc. For example, if water is running constantly, the equipment operator 716 could identify a fault. Similarly, if the water usage of a valve is greater than a particular level, the equipment operator 716 could identify a fault.

The building health manager 128 includes an interface generator 718. The interface generator 718 is configured to generate user interfaces and cause the user interfaces to display on the user device 728. The user device 728 may be the same as, or similar to, the user device 148 of FIG. 1. For example, the interface generator 718 can generate the user interfaces of FIGS. 8 and 9 and cause a display device of the user device 728 to display the user interfaces. A user, via an interface of the user device 728, can provide input via the user interface which can be receive by the building health manager 128. In some embodiments, the user interfaces displayed by the user device 728 can display recommendations for changing the operation of the building system 730 (e.g., run UV lights, increase air changes for a building, etc.). A user can interface with the recommendation via the user device 728 to implement the operation.

Figure 8:
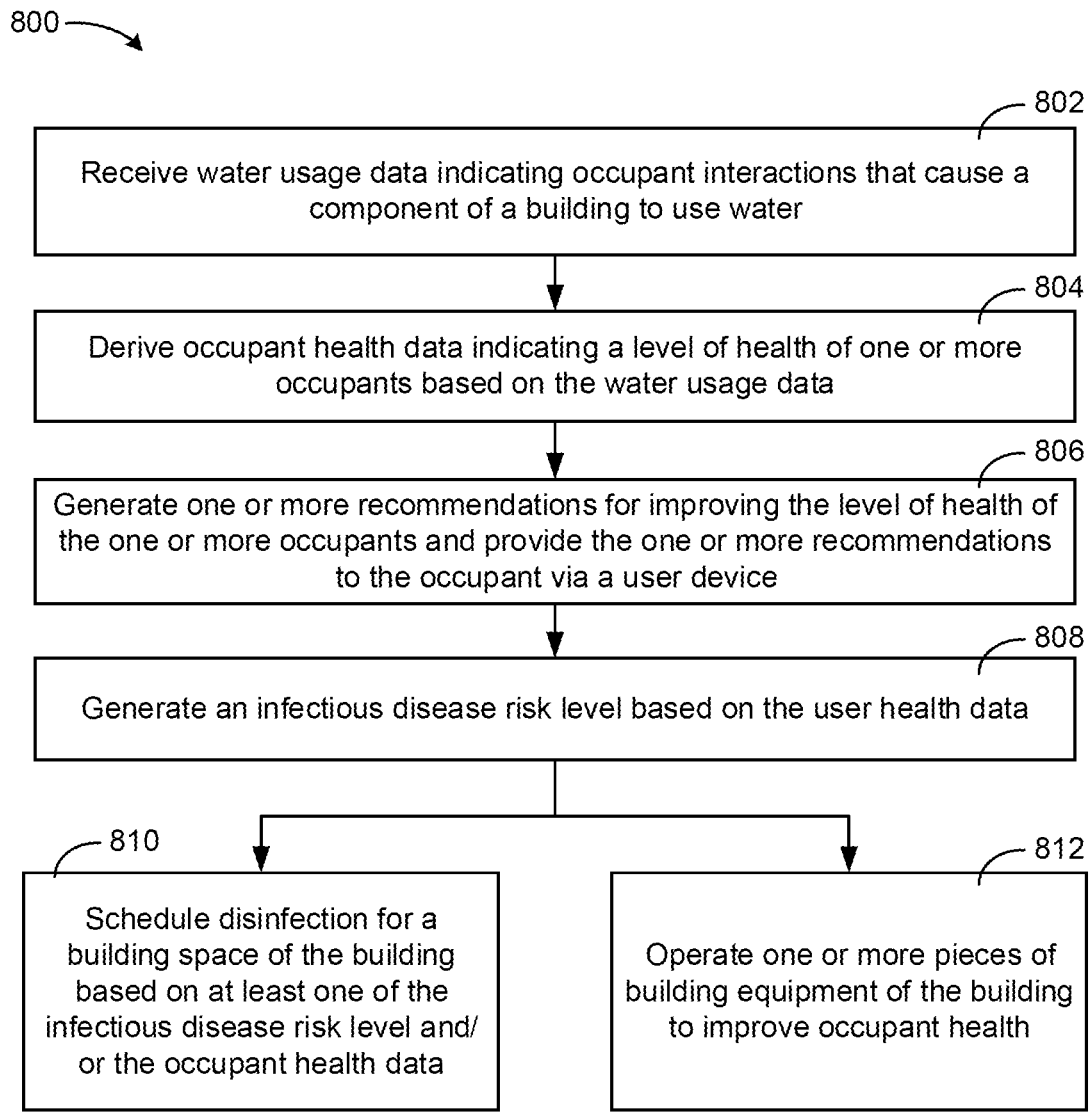
FIG. 8 is a flow diagram of a process of generating occupant health data based on valve data received from the connected water valves of FIG. 6, according to an exemplary embodiment.

Referring now to FIG. 8, a process 800 of generating occupant health data based on valve data received from the connected water valves 602-630 is shown, according to an exemplary embodiment. In some embodiments, the building health manager 128 is configured to perform the process 800. In some embodiments, any computing device described herein can be configured to perform the process 800.

In step 802, the building health manager 128 receives water usage data indicating interactions that cause a component of a building to use water. For example, the water usage data can indicate that a toilet or urinal has been flushed at a particular time in a particular bathroom of a building and that a particular amount of water has been used in the flush. In some embodiments, the flush event can further indicate an identify of a user that performed the flush. The water usage data can indicate that a faucet has been run at a particular time in a particular bathroom of a building and that a particular amount of water has been used in the faucet run. In some embodiments, the faucet run event can further indicate an identify of a user that performed the faucet run. The faucet run event in a bathroom can indicate that a user has washed their hands. The water usage data can indicate that water drinking fountain has been run at a particular time in a particular area of a building and that a particular amount of water has been used by the drinking fountain. In some embodiments, the data can further indicate an identify of a user that drank water from the water drinking fountain.

In step 804, the building health manager 128 can derive occupant health data indicating a level of health of one or more occupants based on the water usage data. For example, the building health manager 128 can take a ratio of bathroom toilet or urinal flush and handwashing events. This data can indicate cleanliness with respect to washing hands. Similarly, the building health manager 128 can take a ratio of toilet or urinal flushes to number of occupants to see the frequency at which occupants are going to the bathroom, indicative of the hydration levels of the occupants. Furthermore, the building health manager 128 can generate a ratio of water fountain drinking events to number of occupants in the space.

In some embodiments, the building health manager 128 can be configured to track how long each sink runs. In some embodiments, if the sink runs for an ideal amount of time for an occupant to properly wash their hands, the occupant health data can be derived to indicated whether occupants are properly washing their hands.

In some embodiments, the building health manager 128 can determine an occupancy level for a space (e.g., a building, a floor of the building, a zone of the building, a room of the building, etc.). The building health manager 128 can predict an occupancy level for a space with a model. The model may correlate water usage data with occupancy levels. The model could be trained by the building health manager 128 based on training data. For example, a prediction model such as a neural network, a random forest classification, a logistic regression model, etc. could be trained based on correlations between occupancy level, water usage level, time of day, day of week, etc. In some embodiments, the model correlates water usage data and current time to determine occupancy levels. For example, certain times of a day (e.g., early morning, early afternoon, etc.) or certain days (e.g., weekdays compared to weekends) can usually expect higher occupancy levels and thus the water usage data would be expected to be higher during those times.

In step 806, the building health manager 128 generates one or more recommendations for improving the level of health of the one or more occupants and provide the one or more recommendations to the occupant via the user device 728. The recommendations can be to schedule cleaning for a space with poor hand washing compliance (e.g., a handwashing ratio of handwashing events to flush events being less than a particular level). Furthermore, the recommendations can be to increase air changes for a space with poor hand washing compliance.

In step 808, the building health manager 128 can generate an infectious disease risk level. The infectious disease risk level can indicate a risk of spreading an infection in a building space. In some embodiments, the infectious disease risk level can be based on the presence of an infectious disease in an area that a building is located. The infectious disease risk level can be based on the hydration levels of occupants of a building, the handwashing cleanliness of occupants of the building, etc. In some embodiments, the building health manager 128 can receive social media data from a social media server indicating buzz words such as "sick, "cold," "not feeling well," etc. The building health manager 128 can generate the infectious disease risk level based, in part, on the frequency of disease related buzz words in the social media data.

In step 810, the building health manager 128 can schedule disinfection for a building space of the building based on at least one of the infectious disease risk level and the water usage data. The disinfection for the building space can be scheduled based on high infectious disease risk levels and/or poor handwashing cleanliness for the building space. The disinfection can be manual maintenance cleaning, UV lighting, operating disinfection drones, etc. Furthermore, in step 812, the building health manager 128 can operate one or more pieces of building equipment of the building to improve occupant health. For example, if occupant handwashing cleanliness is low for a particular area of a building, the building health manager can operate one or more pieces of building equipment to improve occupant health, e.g., increase airflow in the building, operate UV lights, etc. In some embodiments, the building health manager 128 can use the occupant health data or infectious disease risk level to negotiate insurance rates for the building with an insurance provider.

Figure 9:
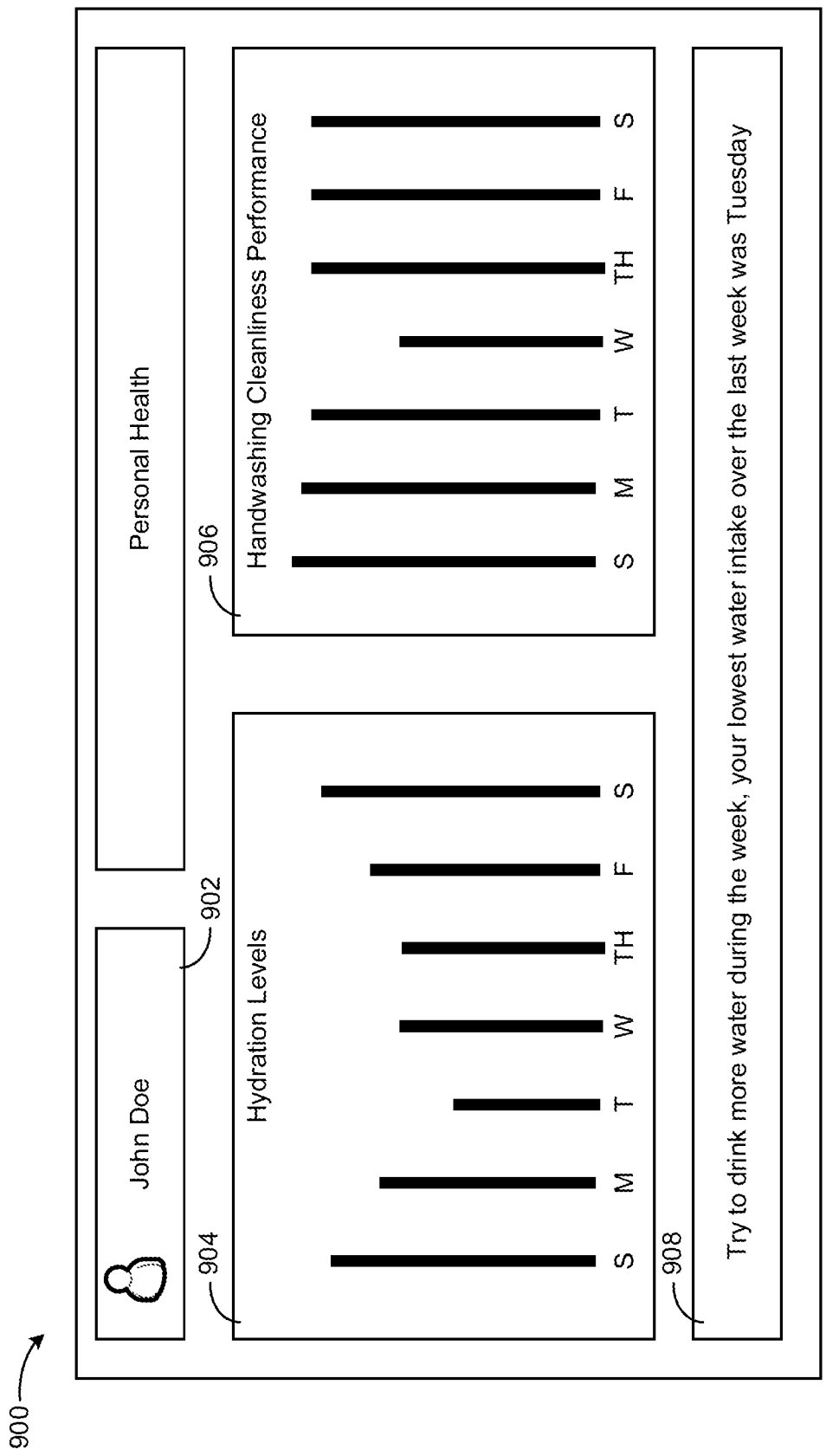
FIG. 9 is a user interface including occupant health data generated from the valve data of the connected water valves of FIG. 6 for a particular occupant, according to an exemplary embodiment.

Referring now to FIG. 9, a user interface 900 including occupant health data generated from the valve data of the connected water valves 602-630 for a particular occupant is shown, according to an exemplary embodiment. In some embodiments, the interface generator 718 receives data from the health analyzer 701, generates the user interface 900 based on the received data, and causes a display device of the user device 728 to display the user interface 900.

The user interface 900 is a user interface for a specific occupants and provides occupant related information specific to an occupant. The interface 900 includes an identification of the user in element 902. Element 904 is a bar chart providing hydration levels recorded by the health analyzer 701 for various days. Similarly, the user interface 900 includes a handwashing cleanliness performance 906 indicating handwashing scores for the occupant for various days. Furthermore, in the interface 900, a recommendation 908 is displayed specific for the user, i.e., to drink more water during on Tuesdays since the hydration levels of the user is falling on Tuesdays.

Figure 10:
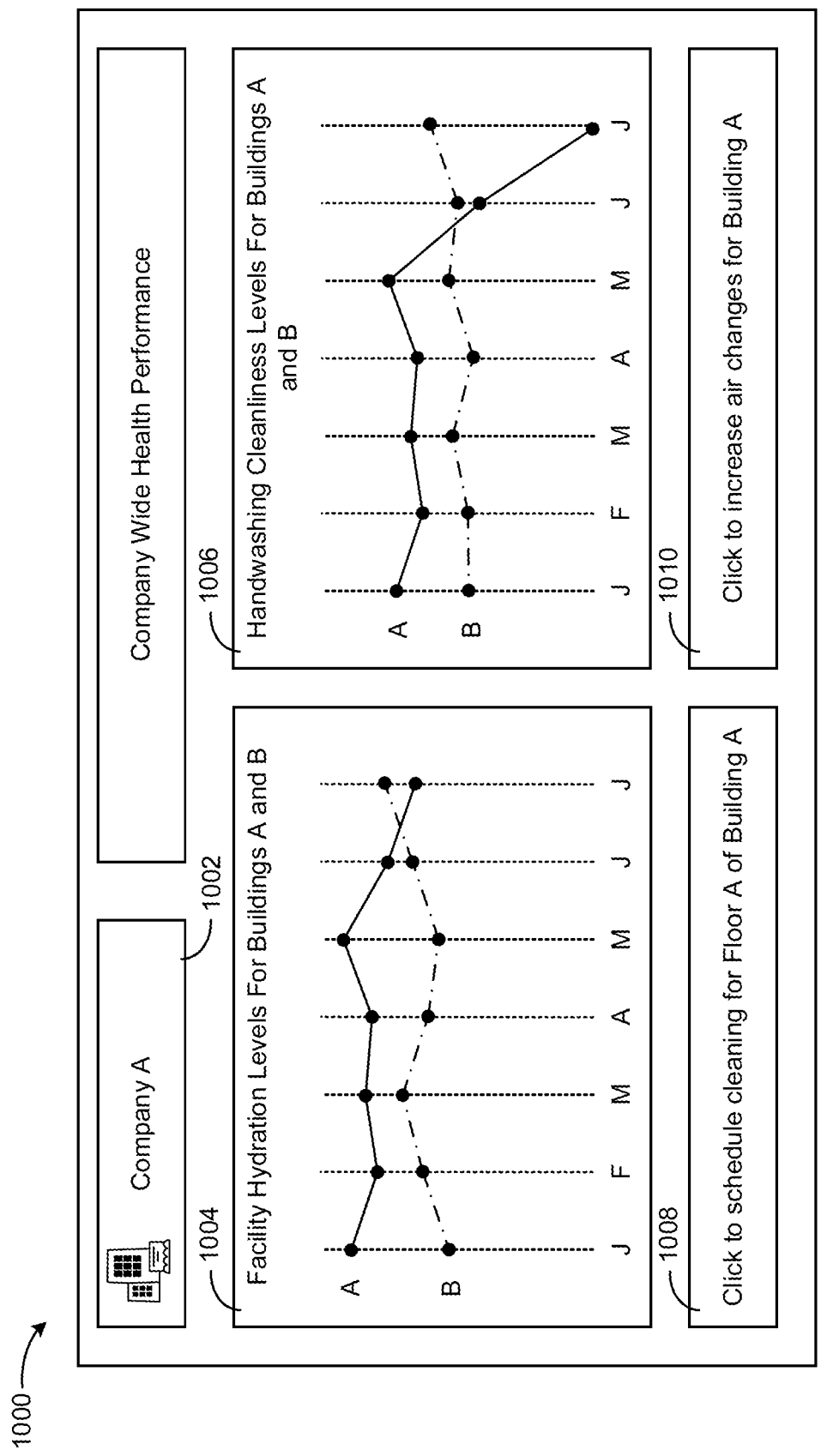
FIG. 10 is a user interface including occupant health data generated from the valve data of the connected water valves of FIG. 7 for particular buildings, according to an exemplary embodiment.

Referring now to FIG. 10, a user interface 1000 including occupant health data generated from the valve data of the connected water valves 602-630 for particular buildings is shown, according to an exemplary embodiment. In some embodiments, the interface generator 718 receives data from the health analyzer 701, generates the user interface 900 based on the received data, and causes a display device of the user device 728 to display the user interface 1000.

The user interface 1000 is a user interface for a specific occupants and provides occupant related information specific to an occupant. The interface 1000 includes an identification of an entity (e.g., company, organization, etc.) in element 1002. In element 1004, a trend chart providing hydration levels recorded by the health analyzer 701 for various buildings of the entity over months of a year. Similarly, the user interface 1000 includes a handwashing cleanliness performance 1006 indicating handwashing trend scores for the buildings for various months of a year. Furthermore, in the interface 1000, a recommendation 1008 is displayed specific for the entity, i.e., to schedule cleaning for a particular floor of a particular building that is performing low with respect to cleanliness. Furthermore, in the interface 1000, a recommendation 1010 is displayed specific to a specific building. The recommendation 1010 is a recommendation to increase air changes for the building because the handwashing cleanliness levels for the building is low.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

In various implementations, the steps and operations described herein may be performed on one processor or in a combination of two or more processors. For example, in some implementations, the various operations could be performed in a central server or set of central servers configured to receive data from one or more devices (e.g., edge computing devices/controllers) and perform the operations. In some implementations, the operations may be performed by one or more local controllers or computing devices (e.g., edge devices), such as controllers dedicated to and/or located within a particular building or portion of a building. In some implementations, the operations may be performed by a combination of one or more central or offsite computing devices/servers and one or more local controllers/computing devices. All such implementations are contemplated within the scope of the present disclosure. Further, unless otherwise indicated, when the present disclosure refers to one or more computer-readable storage media and/or one or more controllers, such computer-readable storage media and/or one or more controllers may be implemented as one or more central servers, one or more local controllers or computing devices (e.g., edge devices), any combination thereof, or any other combination of storage media and/or controllers regardless of the location of such devices.

What is claimed:

1. A building system of a building comprising one or more memory devices storing instructions thereon that, when executed by one or more processors, cause the one or more processors to:
   receive water usage data from one or more network connected water valves, the water usage data indicating water usage by one or more occupants within the building;
   derive an occupant hydration metric by:
      identifying a number of toilet or urinal flushes based on the water usage data, wherein at least one of the one or more network connected water valves is configured to flush water on a toilet or urinal of a bathroom of the building; and
      identifying the occupant hydration metric based on a number of occupants within the building and the number of toilet or urinal flushes; and
   cause one or more pieces of building equipment to perform one or more operations based on a value of the occupant hydration metric, the one or more operations improving physical health of the one or more occupants.

2. The building system of claim 1, wherein the instructions cause the one or more processors to:
   receive an occupancy level indicating a number of the one or more occupants from an occupancy system that tracks occupancy levels of the building; and
   derive one or more health metrics indicating the physical health of the one or more occupants based on the water usage data and the occupancy level.

3. The building system of claim 1, wherein the instructions cause the one or more processors to:
   determine a number of the one or more occupants with an occupancy model based on the water usage data, wherein the occupancy model correlates a level of the water usage data with the number of the one or more occupants.

4. The building system of claim 1, wherein the instructions cause the one or more processors to:
   determine an infectious disease risk level for the building based on the water usage data, the infectious disease risk level indicating a level of risk of contracting an infectious disease within the building.

5. The building system of claim 1, wherein the instructions cause the one or more processors to:
   identify a first portion of the water usage data associated with a first area of the building;
   identify a second portion of the water usage data associated with a second area of the building;
   derive one or more first health metrics indicating the physical health of the one or more occupants associated with the first area of the building;
   derive one or more second health metrics indicating the physical health of the one or more occupants associated with the second area of the building; and
   cause a display device of a user device to include information associated with the one or more first health metrics and the one or more second health metrics.

6. The building system of claim 1, wherein the instructions cause the one or more processors to:
   receive occupancy data identifying a first occupant and a second occupant;
   identify, based on the occupancy data, first water usage data associated with the first occupant and second water usage data associated with the second occupant;
   derive a first health metric indicating physical health of the first occupant based on the first water usage data;
   derive a second health metric indicating physical health of the second occupant based on the second water usage data; and
   cause a display device of a user device to include information associated with the first health metric and the second health metric.

7. The building system of claim 1, wherein the instructions cause the one or more processors to determine a handwashing cleanliness metric by:
   identifying a number of hand washes based on the water usage data, wherein at least one of the one or more network connected water valves is configured to run water at a handwashing sink of the bathroom; and
   comparing the number of toilet or urinal flushes to the number of hand washes to determine the handwashing cleanliness metric.

8. The building system of claim 1, wherein the instructions cause the one or more processors to:
   schedule cleaning for one or more particular areas of the building based on the occupant hydration metric or one or more health metrics determined based on the water usage data; and
   send a notification of scheduled cleaning to a user device of one or more cleaning personal.

9. The building system of claim 1, wherein the instructions cause the one or more pieces of building equipment to perform the one or more operations based on the value of the occupant hydration metric or values of one or more health metrics determined based on the water usage data by:
   determining that the value of the occupant hydration metric or the values of the one or more health metrics are below a level; and
   causing an air handler unit of the building to increase a level of clean air changes of the building responsive to determining that the value of the occupant hydration metric or the values of the one or more health metrics are below the level.

10. The building system of claim 1, wherein the instructions cause the one or more pieces of building equipment to perform the one or more operations based on the value of the occupant hydration metric or values of one or more health metrics determined based on the water usage data by:
    determining that the value of the occupant hydration metric or the values of the one or more health metrics are below a level; and
    causing an ultraviolet light system of the building to activate and disinfect one or more surfaces of objects of the building responsive to determining that the value of the occupant hydration metric or the values of the one or more health metrics are below the level.

11. The building system of claim 1, wherein the instructions cause the one or more processors to:
    identify a number of water drinking fountain runs based on the water usage data, wherein at least one of the one or more network connected water valves is configured to cause water to run at a water drinking fountain; and
    identify the occupant hydration metric further based on the number of water drinking fountain runs.

12. A method of a building system of a building, comprising:
    receiving, by a processing circuit, water usage data from one or more network connected water valves, the water usage data indicating water usage by one or more occupants within the building;
    deriving, by the processing circuit, an occupant hydration metric by:
        identifying a number of toilet or urinal flushes based on the water usage data, wherein at least one of the one or more network connected water valves is configured to flush water on a toilet or urinal of a bathroom of the building; and
        identifying the occupant hydration metric based on a number of occupants within the building and the number of toilet or urinal flushes; and
    causing, by the processing circuit, one or more pieces of building equipment to perform one or more operations based on a value of the occupant hydration metric, the one or more operations improving physical health of the one or more occupants.

13. The method of claim 12, further comprising:
    determining, by the processing circuit, an infectious disease risk level for the building based on the occupant hydration metric or one or more health metrics determined based on the water usage data, the infectious disease risk level indicating a level of risk of contracting an infectious disease within the building.

14. The method of claim 12, further comprising:
    identifying, by the processing circuit, a first portion of the water usage data associated with a first area of the building;
    identifying, by the processing circuit, a second portion of the water usage data associated with a second area of the building;
    deriving, by the processing circuit, one or more first health metrics indicating the physical health of the one or more occupants associated with the first area of the building;
    deriving, by the processing circuit, one or more second health metrics indicating the physical health of the one or more occupants associated with the second area of the building; and
    causing, by the processing circuit, a display device of a user device to include information associated with the one or more first health metrics and the one or more second health metrics.

15. The method of claim 12, further comprising:
    receiving, by the processing circuit, occupancy data identifying a first occupant and a second occupant;
    identifying, by the processing circuit, based on the occupancy data, first water usage data associated with the first occupant and second water usage data associated with the second occupant;
    deriving, by the processing circuit, a first health metric indicating physical health of the first occupant based on the first water usage data;
    deriving, by the processing circuit, a second health metric indicating physical health of the second occupant based on the second water usage data; and
    causing, by the processing circuit, a display device of a user device to include information associated with the first health metric and the second health metric.

16. The method of claim 12, comprising determining, by the processing circuit, a handwashing cleanliness metric by:
    identifying a number of hand washes based on the water usage data, wherein at least one of the one or more network connected water valves is configured to run water at a handwashing sink of the bathroom; and
    comparing the number of toilet or urinal flushes to the number of hand washes to determine the handwashing cleanliness metric.

17. The method of claim 12, comprising:
    causing, by the processing circuit, the one or more pieces of building equipment to perform the one or more operations based on the value of the occupant hydration metric or values of one or more health metrics determined based on the water usage data comprises:
        determining that the value of the occupant hydration metric or the values of the one or more health metrics are below a level; and
        causing an air handler unit of the building to increase a level of clean air changes of the building responsive to determining that the value of the occupant hydration metric or the values of the one or more health metrics are below the level.

18. One or more memory devices storing instructions thereon that, when executed by one or more processors, cause the one or more processors to:
    receive water usage data from one or more network connected water valves, the water usage data indicating water usage by one or more occupants within a building;
    derive an occupant hydration metric by:
        identifying a number of toilet or urinal flushes based on the water usage data, wherein at least one of the one or more network connected water valves is configured to flush water on a toilet or urinal of a bathroom of the building; and
        identifying the occupant hydration metric based on a number of occupants within the building and the number of toilet or urinal flushes; and
    cause one or more pieces of building equipment to perform one or more operations based on a value of the occupant hydration metric, the one or more operations improving physical health of the one or more occupants.

19. The one or more memory devices of claim 18, wherein the instructions cause the one or more processors to:

identify a first portion of the water usage data associated with a first area of the building;

identify a second portion of the water usage data associated with a second area of the building;

derive one or more first health metrics indicating the physical health of the one or more occupants associated with the first area of the building;

derive one or more second health metrics indicating the physical health of the one or more occupants associated with the second area of the building; and cause a display device of a user device to include information associated with the one or more first health metrics and the one or more second health metrics.

20. The one or more memory devices of claim 18, wherein the instructions cause the one or more processors to determine a handwashing cleanliness metric by:

identifying a number of hand washes based on the water usage data, wherein at least one of the one or more network connected water valves is configured to run water at a handwashing sink of the bathroom; and comparing the number of toilet or urinal flushes to the number of hand washes to determine the handwashing cleanliness metric.

\* \* \* \* \*